US012414717B2

(12) United States Patent
Adler

(10) Patent No.: US 12,414,717 B2
(45) Date of Patent: Sep. 16, 2025

(54) ANALYTE AND ENVIRONMENT SENSORS

(71) Applicant: CANARY MEDICAL SWITZERLAND AG, Baar (CH)

(72) Inventor: Mark A. Adler, Carlsbad, CA (US)

(73) Assignee: Canary Medical Switzerland AG, Baar (CH)

(*) Notice: Subject to any disclaimer, the term of this patent is extended or adjusted under 35 U.S.C. 154(b) by 0 days.

(21) Appl. No.: 19/060,352

(22) Filed: Feb. 21, 2025

(65) Prior Publication Data

US 2025/0235131 A1    Jul. 24, 2025

Related U.S. Application Data

(63) Continuation of application No. 19/058,608, filed on Feb. 20, 2025, which is a continuation of application
(Continued)

(51) Int. Cl.
*A61B 5/145* (2006.01)
*A61B 5/00* (2006.01)
(Continued)

(52) U.S. Cl.
CPC ........ *A61B 5/14735* (2013.01); *A61B 5/0002* (2013.01); *A61B 5/01* (2013.01);
(Continued)

(58) Field of Classification Search
CPC .... A61B 2560/0209; A61B 2560/0223; A61B 2560/045; A61B 2560/0468;
(Continued)

(56) References Cited

U.S. PATENT DOCUMENTS 4,679,562 A    7/1987  Luksha
7,759,073 B2   7/2010  O'Connor et al.
(Continued)

FOREIGN PATENT DOCUMENTS

CN    105380669 A  *  3/2016  ......... A61B 5/14503
JP    2006234458 A     9/2006
(Continued)

OTHER PUBLICATIONS

Franklin R.K., et al., A Comparison of Fabrication Methods for Iridium Oxide Reference Electrodes, IEEE, Sensors, Nov. 2009, pp. 1086-1089.
(Continued)

*Primary Examiner* — Eric J Messersmith

(57) ABSTRACT

Disclosed are devices, systems and methods for in vivo monitoring of localized environment conditions within a patient user by measuring analytes, including glucose, oxygen, and/or other analytes. In some aspects, a sensor device includes a wafer-based substrate, at least one electrochemical sensor two-electrode contingent including a working electrode and a reference electrode on the substrate and configured to detect a target analyte in a body fluid when the sensor device is deployed within a subject's body, where the working electrode is functionalized by a chemical layer configured to facilitate a reaction involving the target analyte that produces an electrical signal; and an electronics unit in communication with the electrochemical sensor electrode contingent to transmit the electrical signal to an external processor.

29 Claims, 9 Drawing Sheets

Related U.S. Application Data

No. 18/726,761, filed as application No. PCT/US2023/010832 on Jan. 13, 2023.

(60) Provisional application No. 63/299,343, filed on Jan. 13, 2022.

(51) Int. Cl.
*A61B 5/01* (2006.01)
*A61B 5/1473* (2006.01)

(52) U.S. Cl.
CPC ........ *A61B 5/1451* (2013.01); *A61B 5/14532* (2013.01); *A61B 5/14546* (2013.01); *A61B 5/6847* (2013.01); *A61B 5/7225* (2013.01); *A61B 5/742* (2013.01); *A61B 2560/0209* (2013.01); *A61B 2560/045* (2013.01); *A61B 2560/0468* (2013.01); *A61B 2562/0271* (2013.01); *A61B 2562/046* (2013.01); *A61B 2562/16* (2013.01); *A61B 2562/18* (2013.01); *A61B 2562/227* (2013.01)

(58) Field of Classification Search
CPC .... A61B 2562/0209; A61B 2562/0271; A61B 2562/046; A61B 2562/16; A61B 2562/18; A61B 2562/227; A61B 5/0002; A61B 5/00; A61B 5/01; A61B 5/073; A61B 5/076; A61B 5/1451; A61B 5/14532; A61B 5/14542; A61B 5/14546; A61B 5/1473; A61B 5/14735; A61B 5/1477; A61B 5/14865; A61B 5/6847; A61B 5/686; A61B 5/7225; A61B 5/742; A61B 5/746; C12Q 1/001
See application file for complete search history.

(56) References Cited

U.S. PATENT DOCUMENTS

| | | | |
|---|---|---|---|
| 7,819,822 B2 | 10/2010 | Calasso et al. | |
| 7,863,035 B2 | 1/2011 | Clemens et al. | |
| 9,056,161 B2 | 6/2015 | Yodat et al. | |
| 10,506,968 B2 | 12/2019 | Heikenfeld et al. | |
| 10,712,309 B2 | 7/2020 | Paul et al. | |
| 10,932,761 B2 | 3/2021 | Heikenfeld | |
| 11,197,627 B2 | 12/2021 | Peterson et al. | |
| 11,259,724 B2 | 3/2022 | Suri et al. | |
| 2003/0199893 A1 | 10/2003 | Boecker et al. | |
| 2005/0123680 A1* | 6/2005 | Kang | A61B 5/14865 600/347 |
| 2006/0070878 A1* | 4/2006 | Wu | G01N 27/3272 204/403.01 |
| 2008/0058625 A1* | 3/2008 | McGarraugh | G01N 33/48792 600/347 |
| 2009/0143660 A1 | 6/2009 | Brister et al. | |
| 2011/0024043 A1 | 2/2011 | Boock et al. | |
| 2011/0027453 A1 | 2/2011 | Boock et al. | |
| 2012/0097554 A1 | 4/2012 | Shah et al. | |
| 2014/0123893 A1 | 5/2014 | Boock et al. | |
| 2016/0081600 A1 | 3/2016 | Simpson et al. | |
| 2017/0079566 A1 | 3/2017 | Rong et al. | |
| 2017/0173262 A1 | 6/2017 | Veltz | |
| 2018/0000388 A1 | 1/2018 | Simpson et al. | |
| 2018/0289296 A1 | 10/2018 | Heikenfeld et al. | |
| 2019/0122884 A1 | 4/2019 | O'Shaughnessy et al. | |
| 2019/0231263 A1* | 8/2019 | Ribet | A61B 5/685 |
| 2019/0307371 A1 | 10/2019 | Boock et al. | |
| 2020/0037938 A1 | 2/2020 | Rong et al. | |
| 2021/0038773 A1 | 2/2021 | Cui et al. | |
| 2021/0100452 A1 | 4/2021 | Brister et al. | |
| 2021/0106281 A1 | 4/2021 | Tran | |
| 2021/0196157 A1 | 7/2021 | Suri | |
| 2021/0341415 A1 | 11/2021 | Yan et al. | |
| 2022/0167886 A1 | 6/2022 | Suri | |
| 2022/0178867 A1 | 6/2022 | Wang et al. | |
| 2022/0211301 A1* | 7/2022 | Suri | A61B 5/1468 |
| 2022/0387991 A1 | 12/2022 | Emaminejad et al. | |
| 2023/0069111 A1 | 3/2023 | Clemente et al. | |
| 2024/0033428 A1* | 2/2024 | Cargill | A61B 5/4839 |

FOREIGN PATENT DOCUMENTS

| | | |
|---|---|---|
| WO | 0059370 A1 | 10/2000 |
| WO | 2005053523 A1 | 6/2005 |
| WO | 2017117416 A1 | 7/2017 |
| WO | 2018065954 A1 | 4/2018 |
| WO | 2018136610 A1 | 7/2018 |
| WO | 2020245312 A1 | 12/2020 |
| WO | 2021119546 A1 | 6/2021 |
| WO | 2021216186 A2 | 10/2021 |
| WO | 2021232109 A1 | 11/2021 |
| WO | 2022026764 A1 | 2/2022 |
| WO | 2022183026 A1 | 9/2022 |

OTHER PUBLICATIONS

Ges I.A., et al., Differential pH Measurements of Metabolic Cellular Activity in nl Culture Volumes using Microfabricated Iridium Oxide Electrodes, Biosensors and Bioelectronics, 2007, vol. 22, pp. 1303-1310.

International Search Report and Written Opinion for International Application No. PCT/US2023/010832, mailed Apr. 18, 2023, 18 Pages.

Nguyen C.M., Design and Fabrication of Iridium Oxide (IROX)-Based Multi-Electrode Array for Biomedical Sensors, The University of Texas at Arlington, May 2015, 123 pages.

Tolosa V.M., et al., Electrochemically Deposited Iridium Oxide Reference Electrode Integrated with an. Electroenzymatic Glutamate Sensor on a Multi-Electrode Array Microprobe, Biosensors and Bioelectronics, 2013, vol. 42, pp. 256-260.

Bauer M., et al., "Electrochemical Multi-analyte Point-of-care Perspiration Sensors Using On-chip Three-dimensional Graphene Electrodes", Analytical and Bioanalytical Chemistry, 2021, vol. 413, pp. 763-777.

Dong Q., et al., "Iridium Oxide Enabled Sensors Applications", Catalysts, 2021, vol. 11, No. 10, 1164, pp. 1-34.

Su L., "Wearable Electrochemical Sensors for Monitoring of Glucose and Electroactive Drugs", International Journal of Electrochemical Science, Aug. 2022, vol. 17, No. 8, 220841, pp. 1-12.

Wang C., et al., "Point-of-care Diagnostics for Infectious Diseases: from Methods to Devices", Nano Today, 2021, vol. 37, 101092, pp. 1-53.

\* cited by examiner

ANALYTE AND ENVIRONMENT SENSORS

CROSS-REFERENCE TO RELATED APPLICATIONS

All applications for which a foreign or domestic priority claim is identified in the Application Data Sheet as filed with the present application are hereby incorporated by reference.

TECHNICAL FIELD

This present disclosure relates to sensors for monitoring one or multiple biomarkers and environmental conditions in vitro, ex vivo or in vivo.

BACKGROUND

There is a need for improved sensors and systems and methods for monitoring one or multiple biomarkers and environmental conditions in vitro, ex vivo or in vivo. The present disclosure addresses those needs.

BRIEF SUMMARY

In brief, disclosed are devices, systems, and methods for in vivo or ex vivo or in vitro monitoring and/or characterizing of one or more parameters of a body fluid from a patient. For example, a body fluid present in the local environment of a patient user into which and/or onto which and/or near which a device of the present disclosure has been implanted and/or placed. As another example, the body fluid may be present in an analytical, e.g., laboratory, equipment, and thus the sensors, devices and systems are used in an in vitro setting. While the devices, systems and methods may be described herein in the context of in vivo analysis, the devices and systems are also applicable to ex vivo and in vitro analysis.

In one embodiment, the device is intended to be implanted at least partially into a patient user for measuring one or more parameters associated with a substance and/or a condition of the local environment where the device is deployed and may be referred to as an in vivo analyte and environment sensor device, or more simply as any of an in vivo sensor device, an in vivo monitoring device, an in vivo analyte sensor device, an environment sensor device, an in vivo sensor, an analyte sensor, an environment sensor, and a sensor device, or the like. In one embodiment, the device is intended to be implanted entirely within a patient user for measuring one or more parameters associated with a substance and/or a condition of the local environment where the device is deployed. In one embodiment, the device is intended to be positioned on a surface, e.g., on the skin of a patient user for measuring one or more parameters associated with a substance and/or a condition of the local environment where the device is deployed. For example, the sensor device may detect and/or measure the concentration of an analyte (i.e., a substance to be identified and/or measured) in the local environment, for example, such as glucose, oxygen, ketones, and/or other analytes. A description of the present technology will primarily refer to an in vivo sensor device that measures parameters or properties of an analyte to illustrate the environment sensor of the present disclosure, which could also be deployed ex vivo. The technology disclosed herein is applicable to monitoring environmental parameters other than analyte identity and concentration. For example, the device may detect and/or measure a temperature of the local in vivo environment that may be indicative of a biological condition, such as infection. As another example, the device may measure the osmolarity and/or osmolality of a fluid in contact with the implanted in vivo environmental sensor.

For example, disclosed are devices, systems and methods for in vivo or ex vivo monitoring of localized environment conditions within or on a patient user by measuring analytes, including glucose, oxygen, and/or other analytes. In some aspects, a sensor device includes a wafer-based substrate, at least one electrochemical sensor two-electrode contingent having a working electrode and a reference electrode on the substrate and configured to detect a target analyte in a body fluid. The sensor device may be deployed within a subject's body. The sensor device may be deployed on a subject's body. The working electrode is functionalized by a chemical layer configured to facilitate a reaction involving the target analyte that produces an electrical signal. The sensor device may also have an electronics unit in communication with the electrochemical sensor electrode contingent to transmit the electrical signal to an external processor.

The following are some exemplary embodiments of the present disclosure, numbered for convenience.

1) A sensor device for monitoring of an analyte, comprising:
   a substrate comprising an electrically non-conductive material;
   an electrochemical sensor electrode contingent disposed on the substrate and configured to detect a target analyte in a body fluid when the electrochemical sensor electrode contingent is deployed fully within a subject's body, the electrochemical sensor electrode contingent comprising, and optionally consisting of, a working electrode and a reference electrode associated with the working electrode, wherein the working electrode is functionalized by a chemical layer configured to facilitate a reaction involving the target analyte that produces an electrical signal at the electrochemical sensor electrode contingent; and optionally
   an electronics unit in communication with the electrochemical sensor electrode contingent, the electronics unit comprising a wireless communications unit including a wireless transmitter or wireless transceiver to transmit data associated with the electrical signal to an external processor, e.g., the sensor device is for in vivo monitoring and includes the optional electronics unit, or the sensor device is for ex vivo monitoring and includes the optional electronics unit, or the sensor device is for in vivo monitoring and does not necessarily include the electronics unit, or the sensor device is for ex vivo monitoring and does not necessarily include the electronics unit.

2) The sensor device of embodiment 1, wherein, the processor is operable to determine a parameter associated with the target analyte based on the electrical signal measured at the electrochemical sensor electrode contingent, and wherein the processor is configured to determine from the same electrical signal produced at the electrochemical sensor electrode contingent a change in an environmental condition within a deployment zone when the electrochemical sensor electrode contingent is deployed within the subject's body.

3) The sensor device of embodiment 2, wherein the change in the environmental condition includes one or more of a change in temperature, a change in moisture, or a change in osmolality.

4) The sensor device of embodiment 2, wherein the change in the environmental condition includes a change in temperature, and wherein the determined change in temperature is indicative of stability of the temperature within the deployment zone and potential infection at least in or proximate the deployment zone.

5) The sensor device of embodiment 2, wherein the change in the environmental condition includes a change in temperature, and wherein the determined change in temperature is informative of a magnitude change of the temperature within the deployment zone.

6) The sensor device of any of embodiments 2-5, wherein the determined change in the temperature is compared to a threshold value to generate an alert when the determined change exceeds the threshold value.

7) The sensor device of embodiment 2, wherein the change in the environmental condition includes a change in osmolality, and wherein the determined change in osmolality is indicative of stability of the salt concentration within the deployment zone and potential dehydration at least in or proximate the deployment zone.

8) The sensor device of embodiment 7, wherein the determined change in the osmolality is compared to a threshold value to generate an alert when the determined change exceeds the threshold value.

9) The sensor device of embodiment 1, further comprising:
a plurality of electrodes disposed on the substrate and configured to detect a parameter associated with electrical conductivity of the body fluid across at least two electrodes of the plurality of electrodes when the sensor device is deployed within the subject's body.

10) The sensor device of embodiment 9, wherein the at least two electrodes are configured to operate as an AND gate, such that when the body fluid is in contact with both of the two electrodes, a short circuit occurs across the two electrodes that corresponds to a one and one signal of the AND gate detectable by the sensor device.

11) The sensor device of any of embodiments 9 or 10, wherein at least some electrodes of the plurality of electrodes are at least partially covered by a permeable membrane.

12) The sensor device of embodiment 1, wherein the substrate includes an upper surface having a plurality of ridges to provide a three-dimensional profile to the sensor device.

13) The sensor device of embodiment 12, wherein the substrate is a wafer-based substrate comprising at least one of silicon oxide, germanium, or gallium arsenide.

14) The sensor device of any of embodiments 12 or 13, wherein the electrochemical sensor electrode contingent has a morphology corresponding to the three-dimensional profile.

15) The sensor device of embodiment 14, wherein the working electrode and the reference electrode are disposed over at least a portion of one or more ridges of the plurality of ridges of the substrate.

16) The sensor device of any of embodiments 12 or 13, wherein the chemical layer has a morphology corresponding to the three-dimensional profile.

17) The sensor device of embodiment 1, wherein the reference electrode includes iridium.

18) The sensor device of embodiment 17, wherein the reference electrode includes iridium oxide.

19) The sensor device of any of embodiments 17 or 18, wherein the sensor device is able to maintain a constant and stable reference signal with respect to the detected electrical signal over a period of time of at least 12 months.

20) The sensor device of any of embodiments 17 or 18, wherein the sensor device is operable to detect the target analyte at a low power consumption based on an applied voltage at the reference electrode of less than 300 mV, or less than 285 mv, or less than 175 mV.

21) The sensor device of any of embodiments 17 or 18, wherein the sensor device is configured to prevent detectable interference signals caused by secondary chemistry elements including dopamine, aspirin, acetaminophen, a numbing chemical for pain treatment, or other.

22) The sensor device of embodiment 1, wherein the working electrode includes at least one of platinum, iridium, gold, silver, titanium, single- or multi-walled carbon nanotubes, or an alloy.

23) The sensor device of embodiment 22, wherein the working electrode includes platinum and iridium.

24) The sensor device of embodiment 1, wherein the working electrode is functionalized by the chemical layer configured to interact with the target analyte to facilitate a reaction that results in a change in electrical charge potential or flow at or proximate the surface of the working electrode, such that an electrical signal associated with the reaction is detectable at the working electrode with respect to the reference electrode to measure a parameter associated with the target analyte.

25) The sensor device of embodiment 24, wherein the chemical layer includes a membrane comprising (i) an outer layer exposed to the body fluid configured to regulate permeation of reactive species including the target analyte and (ii) an inner layer coupled between the outer layer and the surface of the working electrode to immobilize a catalyst able to facilitate the reaction by the permeated reactive species for detection of the target analyte at the working electrode.

26) The sensor device of embodiment 24, wherein the chemical layer includes a membrane comprising (i) an outer layer exposed to the body fluid configured to regulate permeation of reactive species including the target analyte and (ii) an inner layer coupled between the outer layer and the surface of the working electrode to immobilize a catalyst able to facilitate the reaction by the permeated reactive species for detection of the target analyte at the working electrode, wherein the membrane includes a plurality of ripples on a top surface of the outer layer.

27) The sensor device of embodiment 26, wherein the membrane includes a thickness of 10 µm or less or of 5 µm to 10 µm.

28) The sensor device of embodiment 26, wherein the plurality of ripples on the top surface of the outer layer includes a height in a range of 10 µm to 20 µm.

29) The sensor device of embodiment 26, wherein the plurality of ripples on the top surface of the outer layer are configured to promote functional longevity of electrochemical sensor electrode contingent based on increased signal stability of the detected electrical signal and prevention of fouling of the working electrode.

30) The sensor device of any of embodiments 26-29, wherein the plurality of ripples of the membrane are formed at least partially by the membrane conformed on a three-dimensional surface of the substrate.

31) The sensor device of embodiment 1, wherein the electronics unit further comprises a signal conditioning unit in communication with the electrochemical sensor electrode contingent via one or more electrical interface components, the signal conditioning unit comprising an electrical circuit configured to process the detected electrical signal by one or more of amplifying the electrical signal, filtering the electrical signal, or converting the electrical signal from analog to digital.

32) The sensor device of embodiment 31, wherein the electronics unit further comprises a data processing unit in communication with the signal conditioning unit, the data processing unit comprising a processor and a memory and configured to process the electrical signal as analyte data representative of one or more parameters of the target analyte.

33) The sensor device of embodiment 1, comprising electrical interconnection wires and electrical interfacing contact sites disposed on the substrate, wherein the electrical interconnection wires are coupled between the electrochemical sensor electrode contingent and the electrical interfacing contact sites.

34) The sensor device of embodiment 33, wherein the electrical interconnection wires disposed on the substrate are hermetically sealed by a non-permeable material that covers the electrical interconnection wires to provide an electrical shield from the body fluid.

35) The sensor device of embodiment 34, wherein the non-permeable material includes at least one of a parylene, a urethane, or a Teflon material.

36) The sensor device of embodiment 1, comprising a casing that encompasses the electronics unit to protect the electronics unit from exposure to the body fluid and that at least partially encompasses the electrochemical sensor electrode contingent such that the working electrode and reference electrode are exposed to the body fluid when the sensor device is deployed in the body of the subject.

37) The sensor device of embodiment 36, wherein the casing includes one or both of flat sides or curved sides to provide a form factor of the sensor device.

38) The sensor device of embodiment 36, wherein the from factor of the sensor device includes at least one of rectangular, a cylindrical, a conical, an elliptical, a pyramidal, a trapezoidal, or a non-uniform shape.

39) The sensor device of embodiment 1, comprising:
  a second electrochemical sensor electrode contingent disposed on the substrate and configured to detect a second target analyte in the body fluid when the second electrochemical sensor electrode contingent is deployed fully within the subject's body, the second electrochemical sensor electrode contingent comprising, and optionally consisting of, a second working electrode and a second reference electrode associated with the second working electrode, wherein the second working electrode is functionalized by a second chemical layer configured to facilitate a reaction involving the second target analyte that produces a second electrical signal at the second electrochemical sensor electrode contingent.

40) The sensor device of embodiment 1, comprising:
  one or more electrically conductive pads disposed on the substrate configured to be electrically stimulated so as to detect parameters associated with the body fluid exposed to the electrochemical sensor electrode contingent.

41) The sensor device of embodiment 40, wherein the one or more electrically conductive pads are capable of ensuring the detected electrical signal is detected in a fluid rich environment.

42) The sensor device of embodiment 40, wherein the one or more electrically conductive pads are capable of decreasing noise associated with the detected signal to a negligible level.

43) The sensor device of any of embodiments 1-42, wherein the target analyte includes one or more of glucose, oxygen, a ketone, water, an amino acid, a nucleic acid, a lipid, a protein, a carbohydrate, a liposome, a nanoparticle, or a pharmacological drug.

44) The sensor device of any of embodiments 1-43, wherein the sensor device is configured to detect the target analyte as a primary biomarker indicative of the subject's health and to detect a secondary biomarker concurrently with the primary biomarker, wherein the secondary biomarker includes a physiological parameter including one or both of temperature and vibration, wherein the physiological parameter is detected based on signal analysis of the detected electrical signal by the electrochemical sensor electrode contingent.

45) The sensor device of any of embodiments 1-44, wherein the sensor device is operable to be inserted below a subcutaneous layer of a subject and within interstitial pocket of the subject such that the sensor contingent is able to detect and determine whether there is a sufficient pool of interstitial fluid in the interstitial pocket to obtain the electrical signal associated with the target analyte.

46) A sensor device for in vivo monitoring of analytes, comprising:
  a substrate comprising an electrically non-conductive material, wherein the substrate is a wafer-based substrate comprising silicon oxide and includes an upper surface having a plurality of ridges to provide a three-dimensional profile to the sensor device;
  an electrochemical sensor electrode contingent disposed on the substrate and configured to detect a target analyte in a body fluid when the electrochemical sensor electrode contingent is deployed fully within a subject's body, the electrochemical sensor electrode contingent comprising, and optionally consisting of, a working electrode and a reference electrode associated with the working electrode, wherein the electrochemical sensor electrode contingent has a morphology corresponding to the three-dimensional profile provided by the substrate, wherein the working electrode is functionalized by a chemical layer configured to facilitate a reaction involving the target analyte that produces an electrical signal at the electrochemical sensor electrode contingent, wherein the reference electrode includes iridium oxide and the working electrode includes platinum and iridium, and wherein the sensor device is operable to detect the target analyte at a low power consumption based on an applied voltage at the reference electrode of less than 300 mV, or less than 285 mv, or less than 175 mV,
  wherein the chemical layer includes a membrane comprising (i) an outer layer exposed to the body fluid configured to regulate permeation of reactive species including the target analyte and (ii) an inner layer coupled between the outer layer and the surface of the working electrode to immobilize a catalyst able to facilitate the reaction by the permeated reactive species for detection of the target analyte at the working electrode, wherein the membrane includes a plurality of ripples on a top surface of the outer layer;
  a plurality of electrodes disposed on the substrate and configured to detect a parameter associated with electrical conductivity of the body fluid across at least two electrodes of the plurality of electrodes when the sensor device is deployed within the subject's body, wherein the at least two electrodes are configured to operate as an AND gate, such that when the body fluid is in contact with both of the two electrodes, a short circuit occurs across the two electrodes that corresponds to a one and one signal of the AND gate detectable by the sensor device; and an electronics unit in communication with the electrochemical sensor electrode contingent, the electronics unit comprising a wireless communications unit including a wireless transmitter or wireless transceiver to transmit data associated with the electrical signal to an external processor, wherein, the processor is operable to determine a parameter associated with the target analyte based on the electrical signal measured at the electrochemical sensor electrode contingent, and wherein the processor is configured to determine from the same electrical signal produced at the electrochemical sensor electrode contingent a change in an environmental condition including temperature within a deployment zone when the electrochemical sensor electrode contingent is deployed within the subject's body.

47) The sensor device of embodiment 46, wherein the sensor device includes one or more features recited in any of embodiments 2-45.

48) A sensor device for in vivo monitoring of analytes, comprising:

a substrate comprising an electrically non-conductive material; and an electrochemical sensor electrode contingent disposed on the substrate and configured to detect a target analyte in a body fluid when the electrochemical sensor electrode contingent is deployed fully within a subject's body, the electrochemical sensor electrode contingent comprising, and optionally consisting of, a working electrode and a reference electrode associated with the working electrode, wherein the working electrode is functionalized by a chemical layer configured to facilitate a reaction involving the target analyte that produces an electrical signal at the electrochemical sensor electrode contingent.

49) The sensor device of embodiment 48, wherein the sensor device includes one or more features recited in any of embodiments 2-45.

50) A sensor device for in vivo monitoring of analytes, comprising:

a substrate comprising an electrically non-conductive material; and an electrochemical sensor electrode contingent disposed on the substrate and configured to detect a target analyte in a body fluid when the electrochemical sensor electrode contingent is deployed fully within a subject's body, the electrochemical sensor electrode contingent comprising a working electrode and a reference electrode associated with the working electrode, wherein the working electrode is functionalized by a chemical layer configured to facilitate a reaction involving the target analyte that produces an electrical signal at the electrochemical sensor electrode contingent, where, optionally, the reference electrode comprises iridium.

51) The sensor device of embodiment 50, wherein the sensor device includes one or more features recited in any of embodiments 2-45.

52) A system for analyte and environment sensing, comprising:

a sensor device operable to be deployed at least partially in a body of a patient user, the sensor device comprising:

a substrate comprising an electrically non-conductive material, an electrochemical sensor electrode contingent disposed on the substrate and configured to detect a target analyte in a body fluid when the electrochemical sensor electrode contingent is deployed fully within a patient user's body, the electrochemical sensor electrode contingent comprising, and optionally consisting of, a working electrode and a reference electrode associated with the working electrode, wherein the working electrode is functionalized by a chemical layer configured to facilitate a reaction involving the target analyte that produces an electrical signal at the electrochemical sensor electrode contingent, and an electronics unit in communication with the electrochemical sensor electrode contingent, the electronics unit comprising a wireless communications unit including a wireless transmitter or wireless transceiver to transmit data associated with the electrical signal to an external processor; and a data processing system, comprising a processor and a memory, in data communication with the sensor device and configured to receive the data from the sensor unit and process the received data to indicate a parameter associated with the target analyte and/or an environmental condition in a region where the electrochemical sensor electrode contingent is deployed.

53) The system of embodiment 52, wherein the sensor device includes one or more features associated with the sensor device recited in any of embodiments 1-45, any of embodiments 46-47, any of embodiments 48-49, and/or any of embodiments 50-51.

54) The system of embodiment 52, wherein the data processing system includes a server computer comprising the processor and the memory and one or more databases in data communication with the server computer, wherein the data processing system is configured to remotely monitor data associated with the patient user obtained by the sensor device.

55) The system of embodiment 52, further comprising:

a receiver device, comprising a processor and a memory, operable to (i) receive a wireless transmission carrying data indicative of the electrical signal acquired from the sensor device and (ii) transmit the data to the data processing system.

56) The system of embodiment 55, wherein the receiver device is configured to store the data in the memory of the receiver device.

57) The system of embodiment 55, wherein the receiver device is in communication with the data processing system via a network of computers in communication with each other and accessible through the Internet.

58) The system of embodiment 52, comprising: further a remote client computing device, comprising a processor and a memory, in data communication with the data processing system and configured to receive processed data that is selected, filtered, and/or formatted by the data processing system.

59) A device, system, or method for in vivo monitoring of at least one analyte and secondary phenomenon, including temperature, in conjunction with the at least one analytes in accordance with the disclosure of this patent document.

60) A sensor device for monitoring an analyte, the sensor device comprising:

a substrate comprising an electrically non-conductive material;

an electrochemical sensor electrode contingent disposed on the substrate and configured to detect a target analyte, the electrochemical sensor electrode contingent comprising two electrodes, and optionally consisting of exactly two electrodes, the two electrodes being a working electrode and a reference electrode;

wherein the working electrode is functionalized by a chemical layer configured to facilitate a reaction involving the target analyte that produces an electrical signal at the electrochemical sensor electrode contingent; and wherein the reference electrode comprises a layer of iridium metal and a layer iridium oxide.

61) The sensor device of embodiment 60 wherein the substrate is a planar wafer comprising silicon dioxide.

62) The sensor device of embodiment 60 wherein the target analyte is glucose, and the working electrode comprises glucose oxidase.

63) The sensor device of embodiment 60 wherein the working electrode comprises a layer of platinum metal and a layer of titanium metal, where the layer of titanium metal is located between the substrate and the layer of platinum metal.

64) The sensor device of embodiment 60 wherein the working electrode comprises a layer of platinum metal and a layer of titanium metal, where the layer of titanium metal is located between the substrate and the layer of platinum metal, where the layer of titanium metal contains at least 95 wt % titanium metal based on the weight of the titanium layer, and the layer of platinum metal contains at least 95 wt % platinum based on the weight of the platinum layer.

65) The sensor device of embodiment 60 wherein the working electrode comprises no more than 5 wt % of a metal other than platinum and titanium.

66) The sensor device of embodiment 60 wherein the reference electrode comprises a layer of platinum metal and a layer of titanium metal, where the layer of titanium metal is located between the substrate and the layer of platinum metal.

67) The sensor device of embodiment 60 wherein the reference electrode comprises a layer of platinum metal and a layer of iridium metal, where the layer of platinum metal is located between the substrate and the layer of iridium metal.

68) The sensor device of embodiment 60 wherein the reference electrode comprises a layer of iridium metal and a layer of iridium oxide, where the layer of iridium metal is located between the substrate and the layer of iridium oxide.

69) The sensor device of embodiment 60 wherein the reference electrode comprises a layer of titanium layer in directed contact with the substrate, a layer of platinum metal in direct contact with the layer of titanium metal, a layer of iridium metal in direct contact with the layer of platinum metal, and a layer of iridium oxide in direct contact with the layer of iridium metal.

70) The sensor device of embodiment 60 wherein
a. the substrate is a wafer comprising silicon dioxide;
b. the working electrode comprises a layer of titanium metal in direct contact with the substrate, a layer of platinum metal in direct contact with the layer of titanium metal, and a chemical layer comprising glucose oxidase configured to facilitate a reaction involving glucose that produces an electrical signal at the electrochemical sensor electrode contingent; and
c. the reference electrode comprises a layer of titanium metal in direct contact with the substrate, a layer of platinum metal in direct contact with the layer of titanium metal, a layer of iridium metal in direct contact with the layer of titanium metal, and a layer of iridium oxide in direct contact with the layer of iridium metal.

71) The sensor device of embodiment 60 further including one or more features recited in any of embodiments 2-45.

72) The sensor device of any of embodiments 61-69 further including one or more features recited in any of embodiments 2-45.

73) The sensor device of embodiment 70 further including one or more features recited in any of embodiments 2-45.

74) The sensor device of embodiment 60, wherein, the processor is operable to determine a parameter associated with the target analyte based on the electrical signal measured at the electrochemical sensor electrode contingent, and wherein the processor is configured to determine from the same electrical signal produced at the electrochemical sensor electrode contingent a change in an environmental condition within a deployment zone when the electrochemical sensor electrode contingent is deployed within the subject's body.

75) The sensor device of embodiment 60, wherein the change in the environmental condition includes one or more of a change in temperature, a change in moisture, or a change in osmolality.

76) The sensor device of embodiment 60, wherein the change in the environmental condition includes a change in temperature, and wherein the determined change in temperature is indicative of stability of the temperature within the deployment zone and potential infection at least in or proximate the deployment zone.

77) The sensor device of embodiment 60, wherein the change in the environmental condition includes a change in temperature, and wherein the determined change in temperature is informative of a magnitude change of the temperature within the deployment zone.

78) The sensor device of any of embodiments 74-77, wherein the determined change in the temperature is compared to a threshold value to generate an alert when the determined change exceeds the threshold value.

79) The sensor device of any of embodiments 1-78, wherein the target analyte includes one or more of glucose, oxygen, a ketone, water, an amino acid, a nucleic acid, a lipid, a protein, a carbohydrate, a liposome, a nanoparticle, or a pharmacological drug.

80) The sensor device of any of embodiments 1-78, wherein the sensor device is configured to detect the target analyte as a primary biomarker indicative of the subject's health and to detect a secondary biomarker concurrently with the primary biomarker, wherein the secondary biomarker includes a physiological parameter including one or both of temperature and vibration, wherein the physiological parameter is detected based on signal analysis of the detected electrical signal by the electrochemical sensor electrode contingent.

81) The sensor device of any of embodiments 1-78, wherein the sensor device is operable to be inserted below a subcutaneous layer of a subject and within interstitial pocket of the subject such that the sensor contingent is able to detect and determine whether there is a sufficient pool of interstitial fluid in the interstitial pocket to obtain the electrical signal associated with the target analyte.

82) A sensor device of embodiment 60 comprising:
a substrate comprising an electrically non-conductive material, wherein the substrate is a wafer-based substrate comprising silicon oxide and includes an upper surface having a plurality of ridges to provide a three-dimensional profile to the sensor device;

an electrochemical sensor electrode contingent disposed on the substrate and configured to detect a target analyte in a body fluid when the electrochemical sensor electrode contingent is contacted with the body fluid, the electrochemical sensor electrode contingent comprising, and optionally consisting of, a working electrode and a reference electrode associated with the working electrode, wherein the electrochemical sensor electrode contingent has a morphology corresponding to the three-dimensional profile provided by the substrate, wherein the working electrode is functionalized by a chemical layer configured to facilitate a reaction involving the target analyte that produces an electrical signal at the electrochemical sensor electrode contingent, wherein the reference electrode includes iridium oxide and the working electrode includes platinum and iridium, and wherein the sensor device is operable to detect the target analyte at a low power consumption based on an applied voltage at the reference electrode of less than 300 mV, or less than 285 mv, or less than 175 mV, wherein the chemical layer includes a membrane comprising (i) an outer layer exposed to the body fluid configured to regulate permeation of reactive species including the target analyte and (ii) an inner layer coupled between the outer layer and the surface of the working electrode to immobilize a catalyst able to facilitate the reaction by the permeated reactive species for detection of the target analyte at the working electrode, wherein the membrane includes a plurality of ripples on a top surface of the outer layer;

a plurality of electrodes disposed on the substrate and configured to detect a parameter associated with electrical conductivity of the body fluid across at least two electrodes of the plurality of electrodes when the sensor device is deployed within the subject's body, wherein the at least two electrodes are configured to operate as an AND gate, such that when the body fluid is in contact with both of the two electrodes, a short circuit occurs across the two electrodes that corresponds to a one and one signal of the AND gate detectable by the sensor device; and an electronics unit in communication with the electrochemical sensor electrode contingent, the electronics unit comprising a wireless communications unit including a wireless transmitter or wireless transceiver to transmit data associated with the electrical signal to an external processor, wherein, the processor is operable to determine a parameter associated with the target analyte based on the electrical signal measured at the electrochemical sensor electrode contingent.

83) The sensor device of embodiment 82, wherein the sensor device includes one or more features recited in any of embodiments 2-45.

84) A sensor device for monitoring of an analyte, comprising:

a substrate comprising an electrically non-conductive material; and an electrochemical sensor electrode contingent disposed on the substrate and configured to detect a target analyte in a body fluid when the electrochemical sensor electrode contingent is in contact with the body fluid, the electrochemical sensor electrode contingent comprising, and optionally consisting of, a working electrode and a reference electrode associated with the working electrode, wherein the working electrode is functionalized by a chemical layer configured to facilitate a reaction involving the target analyte that produces an electrical signal at the electrochemical sensor electrode contingent.

85) The sensor device of embodiment 84, wherein the sensor device includes one or more features recited in any of embodiments 2-45.

86) A sensor device for monitoring of an analyte, comprising:

a substrate comprising an electrically non-conductive material; and an electrochemical sensor electrode contingent disposed on the substrate and configured to detect a target analyte in a body fluid when the electrochemical sensor electrode contingent is contacted with the body fluid, the electrochemical sensor electrode contingent comprising a working electrode and a reference electrode associated with the working electrode, wherein the working electrode is functionalized by a chemical layer configured to facilitate a reaction involving the target analyte that produces an electrical signal at the electrochemical sensor electrode contingent, where, optionally, the reference electrode comprises iridium.

87) The sensor device of embodiment 86, wherein the sensor device includes one or more features recited in any of embodiments 2-45.

88) The sensor device of any of embodiments 1-87 which is sterile.

89) A system for analyte and environment sensing, comprising:

a sensor device as described herein, e.g., a sensor device of any of embodiments 1 to 88 the sensor device comprising:

a substrate comprising an electrically non-conductive material, an electrochemical sensor electrode contingent disposed on the substrate and configured to detect a target analyte in a body fluid when the electrochemical sensor electrode contingent is contacted with the body fluid, e.g., when the sensor is deployed fully within the body of the patient, the electrochemical sensor electrode contingent comprising, and optionally consisting of, a working electrode and a reference electrode associated with the working electrode, wherein the working electrode is functionalized by a chemical layer configured to facilitate a reaction involving the target analyte that produces an electrical signal at the electrochemical sensor electrode contingent, and an electronics unit in communication with the electrochemical sensor electrode contingent, the electronics unit comprising a wireless communications unit including a wireless transmitter or wireless transceiver to transmit data associated with the electrical signal to an external processor; and a data processing system, comprising a processor and a memory, in data communication with the sensor device and configured to receive the data from the sensor unit and process the received data to indicate a parameter associated with the target analyte and/or an environmental condition in a region where the electrochemical sensor electrode contingent is deployed.

90) The system of embodiment 89, wherein the sensor device includes one or more features associated with the sensor device recited in any of embodiments 1-88.

91) The system of embodiment 89, wherein the data processing system includes a server computer comprising the processor and the memory and one or more databases in data communication with the server computer, wherein the data processing system is configured to remotely monitor data associated with the patient user obtained by the sensor device.

92) The system of embodiment 89, further comprising:
a receiver device, comprising a processor and a memory, operable to (i) receive a wireless transmission carrying data indicative of the electrical signal acquired from the sensor device and (ii) transmit the data to the data processing system.

93) The system of embodiment 92, wherein the receiver device is configured to store the data in the memory of the receiver device.

94) The system of embodiment 92, wherein the receiver device is in communication with the data processing system via a network of computers in communication with each other and accessible through the Internet.

95) The system of embodiment 89, further comprising:
a remote client computing device, comprising a processor and a memory, in data communication with the data processing system and configured to receive processed data that is selected, filtered, and/or formatted by the data processing system.

96) A device, system, or method for in vivo monitoring of at least one analyte and secondary phenomenon, including temperature, in conjunction with the at least one analytes in accordance with the disclosure of this patent document.

97) A method for in vivo detecting the presence of an analyte in a biological fluid, the method comprising implanting inside a patient a sensor device as described herein, e.g., a sensor device of any of embodiments 1-88, exposing the sensor device to the biological fluid inside the patient, generating an electric signal by the sensor device that is responsive to the presence of the analyte in the biological fluid, and converting the electric signal to an observable indication of the presence of the analyte in the biological fluid, where optionally the sensor device may capture, display and/or transmit data associated with the electrical signal.

98) A method for ex vivo detecting the presence of an analyte in a biological fluid, the method comprising locating on a surface of a patient a sensor device as described herein, e.g., a sensor device of any of embodiments 1-88, exposing the sensor device to the biological fluid on the surface of the patient, generating an electric signal by the sensor device that is responsive to the presence of the analyte in the biological fluid, and converting the electric signal to an observable indication of the presence of the analyte in the biological fluid, where optionally the sensor device may capture, display and/or transmit data associated with the electrical signal.

99) A method for ex vivo detecting the presence of an analyte in a biological fluid, the method comprising locating on an biological fluid conduit, e.g., a catheter, a sensor device as described herein, e.g., a sensor device of any of embodiments 1-88, exposing the sensor device to the biological fluid contained within the biological fluid conduit, generating an electric signal by the sensor device that is responsive to the presence of the analyte in the biological fluid, and converting the electric signal to an observable indication of the presence of the analyte in the biological fluid, where optionally the sensor device may capture, display and/or transmit data associated with the electrical signal.

100) A method for in vitro detecting the presence of an analyte in a biological fluid, the method comprising locating a sensor device as described herein, e.g., a sensor device of any of embodiments 1-88 at an in vitro location, exposing the sensor device to the biological fluid at the in vitro location, generating an electric signal by the sensor device that is responsive to the presence of the analyte in the biological fluid, and converting the electric signal to an observable indication of the presence of the analyte in the biological fluid, where optionally the sensor device may capture, display and/or transmit data associated with the electrical signal.

The above-mentioned and additional features of the present invention and the manner of obtaining them will become apparent, and the invention will be best understood by reference to the following more detailed description. All references disclosed herein are hereby incorporated by reference in their entirety as if each was incorporated individually.

This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, the drawings, and the claims.

BRIEF DESCRIPTION OF THE DRAWINGS

Many aspects of the present disclosure can be better understood with reference to the following drawings. The features in the drawings are not necessarily to scale, fully shown, or depicted in the same manner as would be physically constructed. Instead, emphasis is placed on clearly illustrating the principles of the present disclosure. The drawings should not be taken to limit the disclosure to the specific embodiments depicted but are for explanation and understanding only.

DETAILED DESCRIPTION

Figure 1A:
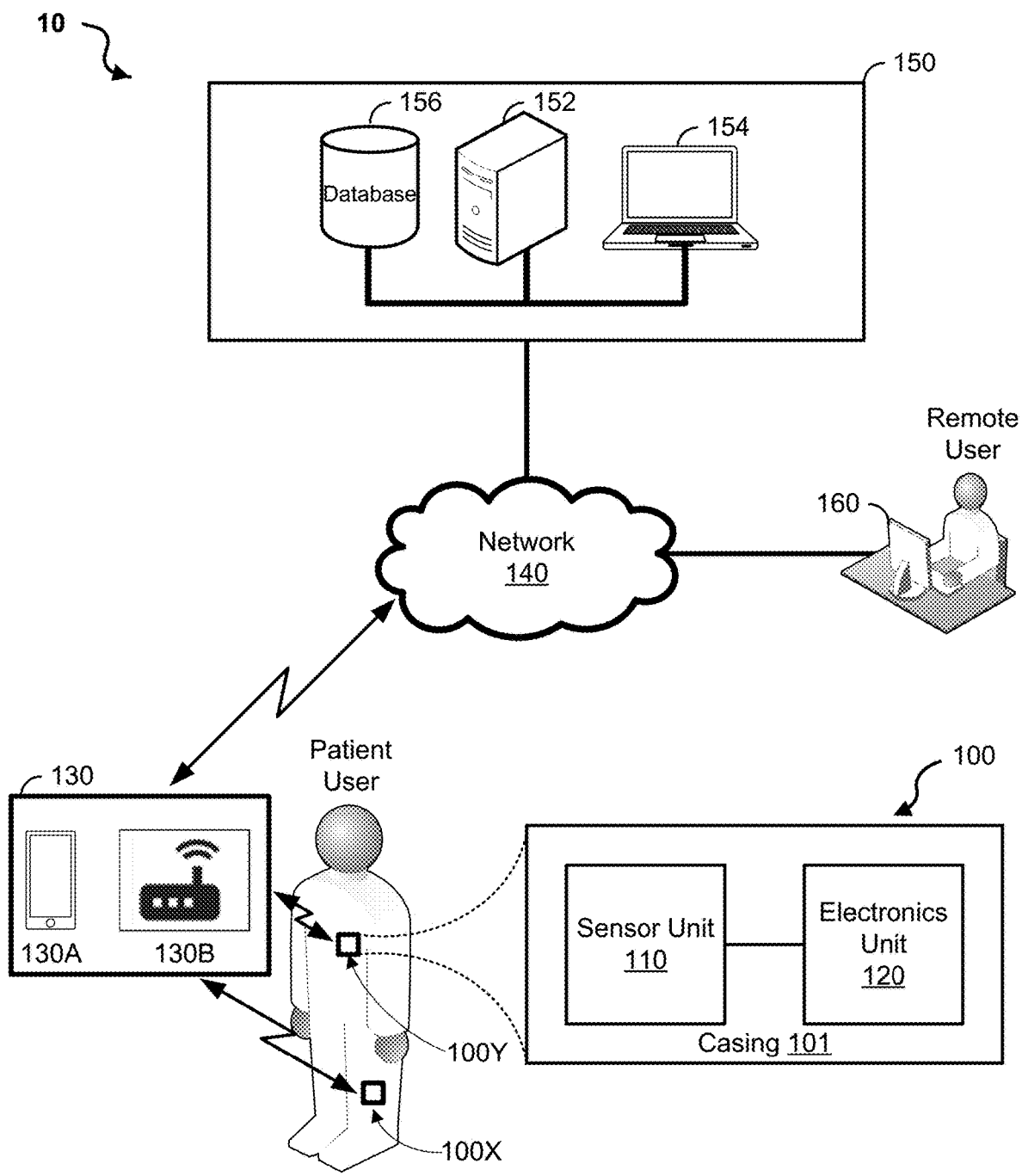
FIG. 1A shows a diagram illustrating an example embodiment of a system for monitoring of one or more analytes of a user, in accordance with the present technology.

Disclosed are devices, systems, and methods for ex vivo and in vivo and in vitro monitoring of one or more parameters of a body fluid of a patient, for example, the local environment of a patient user into which or onto which a device of the present disclosure has been implanted. In one embodiment the device is intended to be implanted at least partially into a patient user for measuring one or more parameters associated with a substance and/or a condition of the local environment where the device is deployed and may be referred to as an in vivo analyte and environment sensor device, or more simply as any of an in vivo sensor device, an in vivo monitoring device, an in vivo analyte sensor device, an environment sensor device, an in vivo sensor, an analyte sensor, an environment sensor, and a sensor device, or the like. For example, the sensor device may detect and/or measure the concentration of an analyte (i.e., a substance to be identified and/or measured) in the local environment, for example, such as glucose, oxygen, ketones, and/or other analytes. A description of the present technology will primarily utilize an in vivo sensor device that measures parameters or properties of an analyte to illustrate the environment sensor of the present disclosure, however technology disclosed herein is applicable to monitoring an environmental parameter in an ex vivo manner or in an in vitro manner. For example, the device may detect and/or measure a temperature of the local in vivo or ex vivo environment that may be indicative of a biological condition, such as infection. As another example, the device may measure the osmolarity and/or osmolality of a fluid in contact with the implanted in vivo environmental sensor.

An in vivo monitoring device, in accordance with the present technology, can include a fully implantable device or a partially implantable device in which at least electrodes of the in vivo monitoring device are inserted within the body of a human or non-human subject to measure one or more target analytes, i.e., a substance having a characteristic capable of being identified and/or measured. An ex vivo monitoring device, in accordance with the present technology, can include a device in which at least electrodes of the monitoring device are located on a surface of the body of a human or non-human subject to measure one or more target analytes, i.e., a substance having a characteristic capable of being identified and/or measured. As mentioned previously, although the sensor device may be referred to herein as suitable for in vivo monitoring, the sensor device may also be suitable for ex vivo monitoring or in vitro monitoring. The terms subject, patient, user, patient user, and the like are used interchangeably herein.

In some aspects the disclosed devices, systems, and methods include a sensor unit, e.g., an in vivo sensor unit or an ex vivo sensor unit, that includes a substrate having a pattern of electrodes. For example, the substrate includes an electrically-insulative (electrically non-conductive) material, and in some embodiments, may be a wafer-based substrate, i.e., a rigid substrate including semiconductor material, such as a crystalline silicon material or non-crystalline (amorphous) silicon material. The pattern of electrodes includes at least one electrochemical sensor electrode assembly (also referred to herein as an electrochemical sensor electrode contingent) including at least one working electrode and at least one reference electrode. The electrochemical sensor electrode contingent may optionally include one, or more than one, additional electrodes, e.g., it may additionally include a counter electrode, or other electrode for electrochemical sensing. In some embodiments, the pattern of electrodes associated with the substrate may include one, two, three, etc. electrochemical sensor electrode contingents, each having the at least one working electrode and the at least one reference electrode, and optionally additional electrode(s). The electrochemical sensor electrode contingent is a component of the sensor unit as described herein. When the pattern of electrodes in an electrochemical sensor electrode contingent is a single two-electrode contingent having a working electrode and reference electrode, the electrochemical sensor electrode contingent may be referred to as a two-electrode electrochemical sensor contingent, or more simply as a two-electrode sensor contingent. When the pattern of electrodes in an electrochemical sensor electrode contingent is a single three-electrode contingent having a working electrode, reference electrode, and counter electrode, the electrochemical sensor electrode contingent may be referred to as a three-electrode electrochemical sensor contingent, or more simply as a three-electrode sensor contingent.

In some embodiments, the electrochemical sensor electrode contingent includes a membrane coupled to the at least one working electrode to provide a sensing region to facilitate a chemical reaction with the one or more target analytes in an in vivo body fluid exposed to the pattern of electrodes, in which the at least one working electrode on the wafer-based substrate is operable to electrochemically detect a product species of the reaction indicative of an analyte parameter. In some embodiments, the at least one reference electrode comprises iridium (e.g., iridium oxide), and the at least one working electrode comprises iridium and/or platinum (e.g., 90/10 platinum/iridium). In some embodiments, the pattern of electrodes provides one or more two-electrode sensor contingent(s) (i.e., a two-electrode sensor contingent does not include a third electrode, e.g., does not include a counter electrode). In some implementations of an iridium-based two-electrode sensor contingent, for example, the electrodes (e.g., iridium-containing working and iridium-containing reference electrodes) is capable of long-term analyte monitoring within the body of the subject, including for 90 days or longer, using a low voltage electrochemical sensing technique in a range of 110 mV to 175 mV, where the target analyte(s) can be detected at an approximate 150 mV threshold.

In some embodiments, for example, the sensor unit includes a pattern of multiple two-electrode sensor contingents, which the sensor unit is operable to monitor multiple analytes, simultaneously, which can be used to determine physiological factors or conditions about the patient user, such as a degree of infection by a foreign substance, e.g., such as a bacterial infection.

In some embodiments, the sensor unit includes one or more electrical conductivity sensors comprising two or more electrodes, which an electrical conductivity sensor can use to determine a fluid presence and/or a fluid property, e.g., osmolarity and/or osmolality. In some embodiments, an electrical conductivity sensor can be operated as a switch that produces a distinguishing signal when the fluid presence is detected (and/or, if in conjunction with an electrochemical sensor electrode contingent, a detectable fluid property meets a predetermined threshold), which, in some implementations, the distinguishable signal may be used as a control signal for certain functionalities of the sensor unit.

In some implementations of the disclosed monitoring devices, example embodiments of the sensor device that include a two-electrode sensor contingent are operable to detect a parameter of the target analyte (e.g., concentration of the analyte in the fluid) while also detecting a change in an environmental condition (e.g., temperature) in the zone or region where the sensor device is located in vivo. As an illustrative example, the disclosed monitoring devices are able to detect occurrence of an infection locally at the site of an incision (e.g., surgical site) from a medical procedure. In implementations where the medical procedure includes inserting an example embodiment of the two-electrode sensor contingent, the in vivo sensor unit can continuously monitor for the target analyte (e.g., glucose) in the subject and, from the same measured signal associated with the target analyte being monitored, can continuously monitor for changes in temperature (and/or other environmental conditions) that are indicative of a surgical site infection (SSI).

As an example, in some implementations, an analyte sensor device in accordance with the disclosed technology can be configured for multi-analyte in vivo or ex vivo monitoring of glucose and a second analyte, e.g., in any mammal, from which the sensed glucose data is processed to create information about health or disease parameters or conditions of the subject, including but not limited to, diabetes and obesity as primary outcomes of the information, and the sensed glucose with the sensed second analyte data is processed to determine information about the subject's nutrient balance, cholesterol, or other factors as secondary outcomes. For example, the example multi-analyte glucose sensor device can be configured to sense oxygen or ketone analytes, and thereby be used in monitoring the operation of a co-implanted medical device, such as an embolic device (i.e., a device that inhibits fluid flow) to determine whether the embolic device is effectively achieving embolic/clotting body formation and performance in vessels of the body.

While disclosed embodiments of an in vivo analyte sensor are described herein primarily based on monitoring of the analyte glucose within a patient's body to facilitate understanding of the underlying concepts of the present technology, it is understood that the disclosed embodiments in accordance with the present technology can also include monitoring of other analytes, including but not limited to, oxygen, ketones, alcohol, water, salts, or other analytical substances. It is also understood that the in vivo analyte sensor may alternatively be an ex vivo analyte sensor which the sensor device is placed on a surface of a subject.

In some embodiments, for example, a sensor device for monitoring of analytes includes a substrate comprising an electrically non-conductive material; an electrochemical sensor electrode contingent disposed on the substrate and configured to detect a target analyte in a body fluid when the electrochemical sensor electrode contingent is deployed (e.g., fully deployed) within a subject's body, the electrochemical sensor electrode contingent has two electrodes, i.e., a working electrode and a reference electrode associated with the working electrode, wherein the working electrode is functionalized by a chemical layer configured to facilitate a reaction involving the target analyte that produces an electrical signal at the electrochemical sensor electrode contingent. The sensor device may also include an electronics unit in communication with the electrochemical sensor electrode contingent, the electronics unit comprising a wireless communications unit including a wireless transmitter or wireless transceiver to at least transmit the electrical signal to an external processor.

These and other embodiments are discussed in greater detail by the examples below.

Example Embodiments

FIG. 1A shows a diagram illustrating an example embodiment of a system 10 for in vivo or ex vivo monitoring of one or more analytes of a patient user, in accordance with the present technology. The system 10 includes one or more analyte sensor devices 100 that can be implanted within the patient user and a data processing system 150 in communication with the one or more analyte sensor devices 100. In some embodiments, the system 10 includes a receiver device 130 operable to receive a wireless transmission carrying data indicative of detected signals acquired from the one or more analyte sensor devices 100 and to transmit and/or store the data to the data processing system 150. In some embodiments, the one or more analyte sensor devices 100 and/or the receiver device 130 is in communication with the data processing system 150 via a network 140 of computers in communication with each other and accessible through the Internet (e.g., referred to as the cloud), where the data from the one or more in vivo analyte sensor devices 100 and/or the receiver device 130 can be transferred to the data processing system 150. Similarly, information from the data processing system 150 can be transferred to the receiver device 130 and/or the one or more analyte sensor devices 100.

The analyte sensor device 100 includes a sensor unit 110 and an electronics unit 120, which are secured in a housing or casing 101. The casing 101 is configured to shield components of the sensor unit 110 and/or the electronics unit 120 from fluids or substances of the body when the in vivo analyte sensor device 100 is deployed inside the patient user.

In the example of the system 10 illustrated in FIG. 1A, the one or more analyte sensor devices 100 includes a first analyte sensor device 100Y deployed in a first portion of the patient user's body, e.g., the head, torso, an appendage, or other area, which may or may not be coupled to an implant device deployed in the patient user's body, such as an implant for the heart, lung, cranium, neck, intestines and digestive track, etc.; and the one or more analyte sensor devices 100 includes a second analyte sensor device 100X deployed in a second portion of the patient user's body, e.g., an extremity, which may or may not be coupled to a second implant device, such as a knee implant device.

In some example implementations, the one or more analyte sensor devices 100 can be placed directly in communication with a fluid-carrying body, such as a blood vessel; where in some implementations, the one or more analyte sensor devices 100 can be placed in the hypodermis layer of skin, e.g., subcutaneous tissue above the muscle tissue and below hair follicles.

In some implementations, for example, the one or more analyte sensors 100 are configured to detect both (i) the target analyte as a primary biomarker indicative of the subject's health and (ii) a secondary biomarker also indicative of the subject's broader health and/or a specific health condition, such as an infection, where the secondary biomarker is detected concurrently with the primary biomarker.

Examples of the secondary biomarker include a physiological parameter, e.g., such as temperature and/or vibration at the body region where the in vivo analyte sensor 100 is deployed within the patient user. In such implementations, the physiological parameter can be detected based on signal analysis of the detected electrical signal by the electrochemical sensor electrode contingent.

In some example embodiments, such as those discussed later in connection with FIG. 1B, the sensor unit 110 includes one or more electrochemical sensor electrode contingents that include at least two electrodes, i.e., a working electrode and a reference electrode, which are configured with respect to the casing 101 such that a body fluid containing a target analyte can be exposed to the at least two electrodes of the sensor unit 110. For example, in some embodiments, the at least two electrodes of the sensor unit 110 are positioned on an outer surface of the casing 101, where other components of the sensing unit (e.g., such as electrically interfacing contacts) are disposed within the casing 101. The sensor unit 110 is electrically coupled to the electronics unit 120, e.g., via electrical interfacing contacts, to provide acquired electrical signals associated with continuous monitoring of the target analyte by the electrochemical sensor electrode contingent(s) to, for example, a signal conditioning unit and/or wireless communications unit of the electronics unit 120, for subsequent data processing. Further details of the sensor unit 110 and the electronics unit 120 for some embodiments of the in vivo analyte sensor device 100 are discussed in FIG. 1B and other figures.

Referring to FIG. 1A, in some implementations, the one or more in vivo analyte sensor devices 100 wirelessly communicate the acquired data obtained directly to the receiver device 130. For example, the one or more analyte sensor devices 100 can transfer the data to the receiver device 130 using a low power wireless communication protocol, e.g., such as Bluetooth Low Energy (BLE), Near Field Communication (NFC), low frequency radio frequency (RF) signal in a range of 3 kHz to 1.3 MHz, or other. Example embodiments of the receiver device 130 include a computing device 130A or a dedicated base station 130B. For example, the computing device 130A can include, but is not limited to, a smartphone, tablet, a wearable computing device (e.g., smartwatch, smart-glasses or headgear, etc.), a laptop or desktop computer, or other. The dedicated base station 130B can include data storage and/or data communication units that facilitate the communication of data from the one or more analyte sensor devices 100 to the data processing system 150 through a Wi-Fi access or cellular link to the network 140. In some implementations, for example, the receiver device 130 can be embodied on multiple receiver devices, such both the computing device 130A (e.g., smartphone, tablet, etc.) and the dedicated base station 130B, as illustrated in the example of FIG. 1A. In some implementations, for example, the receiver device 130 can (i) process, at least partially, the received data for display on a display screen of the receiver device 130 and/or for transfer of the received data to an external computer or computing system, such as the data processing system 150. In some embodiments, for example, the system 10 optionally includes a software application ("app") that is resident on the receiver device 130 to control various data processing, storage, and communication functionalities for management of the received data.

In the example of the system 10 illustrated in FIG. 1A, the data processing system 150 can include one or more server computer devices 152, one or more client computer devices 154, and/or one or more databases 156, in data communication with each other. In implementations, for example, the computer device(s) 152, 154 and the database(s) 156 are in communication with each other and/or in communication with the other devices of the system 10 via the network 140. In some implementations, for example, the data processing system 150 can remotely monitor data associated with the patient user obtained by the one or more analyte sensor devices 100 and/or remotely operate aspects of the system 10, e.g., such as modify sensing parameters or protocols of the one or more in vivo analyte sensor devices 100, data display or processing features of the app on the receiver device 130, or other.

In some embodiments, for example, the system 10 optionally includes a remote computing device 160 operated by a remote user to remotely monitor data associated with the patient user obtained by the one or more analyte sensor devices 100 that is transferred to the data processing system 150. For example, the remote computer 160 can include a personal computer such as a desktop or laptop computer, a mobile computing device such as a smartphone, tablet, smartwatch, etc., or other computing device. In some implementations, for example, the remote computing device 160 is configured to only receive data that is curated (e.g., selected, pre-processed, and/or formatted) by the data processing system 150. In some implementations, for example, the remote computing device 160 is configured to remotely operate one or more aspects (e.g., functionalities) of the system 10. For example, the remote computing device 160 can implement a remote user software application (remote user app) that is configured to provide the remote user with such display, storage, and/or management features. The remote user, for example, can include a health care provider (HCP), such as a physician, nurse, family member of the patient user, or other caregiver, or a medical insurance payer, or other type of stakeholder entity or individual with respect to the patient user's health.

Figure 1B:
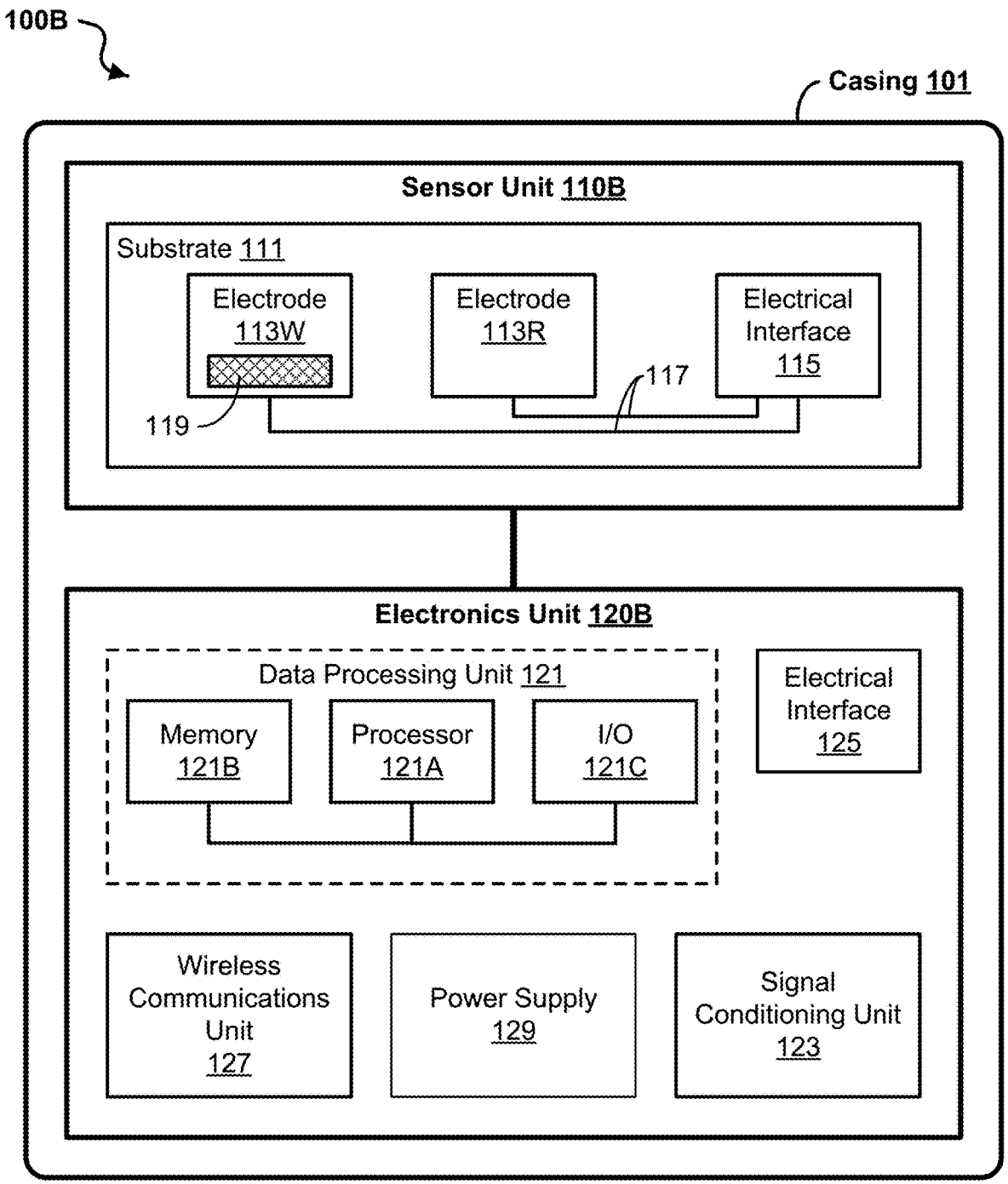
FIG. 1B shows a block diagram illustrating an example embodiment of an analyte sensor of FIG. 1A, in accordance with the present technology.

FIG. 1B shows a block diagram illustrating an example embodiment of the analyte sensor 100 shown in FIG. 1A, shown in FIG. 1B as analyte sensor 100B. In the example of FIG. 1B, the analyte sensor 100B includes an example embodiment of a sensor unit 110 (shown as sensor unit 110B) and an example embodiment of electronics unit 120 (shown as electronics unit 120B). The sensor unit 110B of the analyte sensor 100B includes a substrate 111, a plurality of electrodes 113 arranged on the substrate 111, an electrical interface 115 comprising a plurality of electrical contact sites (e.g., pads, pins, etc.), and a plurality of interconnections 117 disposed on the substrate 111 and configured to couple the electrodes 113 to respective contact sites of the electrical interface 115. In some embodiments, for example, at least some of the plurality of electrodes 113 are configured as electrochemical sensor electrodes to detect an electrical signal corresponding to a reaction involving a target analyte in a fluid exposed to the electrodes 113. In some embodiments, for example, the plurality of electrodes 113 includes a pattern of electrodes including at least one working electrode 113W and at least one reference electrode 113R, e.g., without a counter electrode associated with the sensor contingent.

In various embodiments, for example, the substrate 111 can be configured as a wafer-based substrate that is rigid, electrically insulative, and comprises a semiconductor material, such as a crystalline silicon material or non-crystalline (amorphous) silicon material. The wafer-based substrate can be configured of a certain size and/or geometry, such that one or multiple patterns of electrodes can be fabricated on a single wafer. In some embodiments of the substrate 111, for example, a wafer-based substrate includes silicon oxide (e.g., silica, glass, or other), germanium (e.g., undoped or doped), gallium arsenide, or other.

In various embodiments, for example, the at least one reference electrode 113R comprises iridium (e.g., iridium oxide), and the at least one working electrode 113W comprises iridium and/or platinum (e.g., 90/10 platinum/iridium). For example, in embodiments of the sensor unit 110 where the at least one reference electrode 113R comprises iridium (e.g., an iridium oxide surface of the reference electrode), the iridium-based reference electrode can provide longevity, stability, and protection for the analyte sensor device 100 to detect the target analyte. In implementations, for example, the iridium-based reference electrode is resistant to breakdown of the electrode from reactive species in the fluid (e.g., hydrogen peroxide), which denigrate and ultimately destroy conventional Ag/AgCl reference electrodes. This resistance to breakdown affords the sensor unit 110 several advantages, as compared to conventional electrochemical sensors, e.g., including prevention of substantial sensor drift thus, mitigating a need for recalibrations of the sensor unit 110 and increased use (longevity) of sensor unit 110 in a single deployment in vivo, including up to or beyond 1 year. Moreover, implementations of the sensor unit 110 having the iridium-based reference electrode allows for lower operating voltage potential across the working-reference electrodes, e.g., an operating voltage potential in a range of 100 mV to 200 mV, which in turn allows for lower power consumption of the overall sensor device (e.g., which further mitigates concerns of battery changes or charging) and enables embodiments of the in vivo analyte sensor 100 to be designed with a smaller size or optimal geometry (e.g., since smaller batteries may be used. Furthermore, the lower operating voltage potential across the electrodes prevents the sensor unit 110 from suffering from signal interference from other constituents in the fluid, e.g., caused by secondary chemistry effects on the analyte sensing. Examples of such interference constituents include, but are not limited to, dopamine, aspirin, acetaminophen, or other.

In some embodiments, for example, the at least one working electrode 113W can be functionalized by a chemical layer 119 to interact with the target analyte to facilitate a reaction that results in a change in electrical charge potential and/or flow at or proximate the surface of the at least one working electrode 113W, such that an electrical signal associated with the reaction is detectable at the at least one working electrode 113W with respect to the at least one reference electrode 113R to measure a parameter associated with the target analyte. In some embodiments, the chemical layer 119 can include a membrane configured to provide a restrictive domain that controls the flux of the target analyte and/or other analytes or reactive species in the body fluid exposed to the membrane-coated at least one working electrode 113W.

One example of a membrane as the chemical layer 119 includes a multi-layered membrane comprising an outer layer exposed to the body fluid that regulates permeation of reactive species and an inner layer coupled between the outer layer and the surface of the at least one working electrode 113W to immobilize a catalyst (e.g., enzyme, mediator, etc.) to facilitate a reaction by the permeated reactive species for detection of the target analyte. For example implementations of in vivo glucose monitoring using a peroxide-based glucose sensor, the chemical layer 119 can include glucose oxidase (GOx) entrapped in the inner layer of the example membrane, such that as glucose ($C_6H_{12}O_6$) and oxygen ($O_2$) permeate through the outer layer of the membrane, the glucose and oxygen react in the presence of the catalyst GOx to form gluconic acid ($C_6H_{12}O_7$) and hydrogen peroxide ($H_2O_2$) (and/or gluconolactone ($C_6H_{10}O_6$) and $H_2O_2$ in reactions also including water ($H_2O$)), where the hydrogen peroxide product dissociates to oxygen and charge carriers (hydrogen cations and electrons) and produce a signal current that is measured as proportional to the glucose in the reactions. Examples of the multi-layered membrane include those described in U.S. Patent Publication No. 2021/096157A1, titled "Chemically Fused Membrane for Analyte Sensing", incorporated herein by reference.

Also shown in the example of FIG. 1B, the electronics unit 120B of the analyte sensor device 100B includes a signal conditioning unit 123, a power supply 129, a wireless communications unit 127, and an electrical interface 125, which can include electrically conductive contact sites (e.g., pads, pins, or other contact configuration) that electrically interfaces with the electrical interface 115 of the sensor unit 110B. The electronics unit 120B is configured to receive and at least partially process electrical signals acquired from the one or more electrochemical sensor electrode contingents of the sensor unit 110B. For example, the electrical signals are received at the corresponding contact sites of the electrical interface 125 (via the electrical interface 115) and provided to the signal conditioning unit 123 to improve the quality of the acquired electrical signals from the sensor unit 110B. In such implementations, the output of the signal conditioning unit 123 can include data associated with the signal-processed electrical signals, to be wirelessly transmitted to an external device by the wireless communications unit 127. In example embodiments of the electronics unit 120B, the power supply 129 can include a battery, fuel cell or other power source to supply power to the components of the electronics unit 120B and/or the sensor unit 110B.

In some embodiments, for example, the signal conditioning unit 123 can include a circuit including one or more filters and/or one or more amplifiers to augment the raw electrical signals detected by the at least two electrodes of the sensor unit 110B to increase a signal-to-noise ratio (SNR) of the electrical signals, thereby producing data containing the signal-processed electrical signals. In some embodiments, the signal conditioning unit 123 can include drive circuitry to produce operating electrical signals that generate electrical potentials and/or currents at the electrochemical sensor electrode contingent(s) of the sensor unit 110B for operating an electrochemical sensing technique to be performed at electrode(s) in implementations of the analyte sensor 100B for detecting the target analyte.

In some embodiments, the wireless communications unit 127 includes a wireless transmitter, receiver, and/or transceiver device including an antenna, which is capable of communicating with an external device to communicate raw, partially-processed, or fully-processed data from the signal conditioning unit 123 (and/or the data processing unit 121, discussed below). For example, the wireless communications unit 127 can be configured to manage the communication protocol for transmission or reception via the antenna. An example transceiver unit can include a BLE chipset to communicate with a BLE-enabled device, e.g., a smartphone, tablet, or other external computing device, such as of the receiver device 130.

In some embodiments, the electronics unit 120B optionally includes a data processing unit 121 to at least partially process the conditioned electrical signals to (i) produce data, e.g., in an analog or a digital form, and/or (ii) control functionality of the electronics unit 120B and/or the sensor unit 110B. For example, the data processing unit 121 can be configured to manage data acquisition on data channels associated with the electrodes of the sensor unit 110B. In some embodiments of the data processing unit 121, for example, the data processing unit 121 can include a processor 121A to process data and a memory 121B in communication with the processor 121A to store and/or buffer data. In various embodiments, for example, the processor 121A can include one or multiple processors, and the memory 121B can include one or multiple memory units. For example, the processor 121A can include a central processing unit (CPU), a microcontroller unit (MCU), a graphics processing unit (GPU), or other type of processor. For example, the memory 121B can include and store processor-executable code, which when executed by the processor, configures the data processing unit 121 to perform various operations, e.g., such as receiving information, commands, and/or data, processing information and data, and transmitting or providing information/data to another device. To support various functions of the data processing unit 121, the memory 121B can store information and data, such as instructions, software, values, images, and other data processed or referenced by the processor 121A. For example, various types of random access memory (RAM) devices, read only memory (ROM) devices, flash memory devices, and other suitable storage media can be used to implement storage functions of the memory 121B. In some embodiments, the data processing unit 121 includes an input/output (I/O) unit 121C to interface the processor 121A and/or memory 121B to other modules, units or devices, e.g., associated with an external device, such as the receiver device 130, the data processing system 150, the remote computing device 160, and/or other external devices. In some embodiments, the processor 121A, the memory 121B, and/or the I/O unit 121C is in communication with the wireless communications unit 127, e.g., such as a transmitter (Tx) or a transmitter/receiver (Tx/Rx) unit. For example, in such embodiments, the I/O unit 121C can interface the processor 121A and memory 121B with the wireless communications unit 127, e.g., to utilize various types of wireless interfaces compatible with typical data communication standards, which can be used in communications of the data processing unit 121 with other devices. The data communication standards include, but are not limited to, Bluetooth, Bluetooth Low Energy (BLE), Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE/5G/6G cellular communication methods, and parallel interfaces. In some implementations, the data processing unit 121 can interface with other devices using a wired connection via the I/O unit 121C. The data processing unit 120B can also interface with other external interfaces, sources of data storage, and/or visual or audio display devices, etc. to retrieve and transfer data and information that can be processed by the processor 121A, stored in the memory 121B, or exhibited on an output unit of the receiver device 130 (e.g., smartphone, tablet, etc.) or other external device to the analyte sensor device 100.

In some example embodiments of the analyte sensor device 100B, the analyte sensor device 100B includes two electrochemical sensor electrode contingents, of which the at least two electrodes of each respective electrochemical sensor electrode contingents (i.e., a working electrode and a reference electrode) are disposed on an external side surface of the casing 101, e.g., such as a top wall, bottom wall, or side wall. In some embodiments, for example, an outer surface of the casing 101 that positions the at least two electrodes of each respective electrochemical sensor electrode contingents can include a wall within a cavity region of the casing 101. In various embodiments, for example, the body or form of the example analyte sensor device 100B can have a rectangular geometry; yet, in other examples, the example analyte sensor device 100B can be configured to have curved external walls of the casing 101 and/or various other geometries, including cylindrical, conical, elliptical, pyramidal, trapezoidal, or non-uniform shapes. In some embodiments, the casing 101 can include non-permeable materials, which are rigid or flexible.

In some embodiments, for example, the casing 101 can include one or more coatings. For example, the coating may include a non-permeable material, materials to hermetically seal electrical interconnection components (e.g., electrical interface 115 and interconnections 117) disposed on the substrate 111 to cover the electrical interconnection components and provide an electrical shield from the body fluids, or other. Example coatings of non-permeable material(s) include, but are not limited to, a parylene, a urethane, a silicon, or a polytetrafluoroethylene (e.g., Teflon) material. These coatings may enhance the longevity of the sensor by mitigating (i.e., reducing) bio-degradation and, in some cases, provides a carrier for bio-degradation inhibitors to prolong function and/or provide electronic resilience over time. Examples of bio-degradation inhibitors provided by the coating can include rapamycin, everolimus, or other. Bio-degradation can cause functional change in the performance of the sensor, one example being sensor drift.

Sensor drift, also referred to simply as "drift," occurs when the signal output of the electrochemical sensor loses sensitivity in detecting the target analyte, usually due to break down of materials at the sensor's working and reference electrodes. The drift is the amount of change the signal output undergoes over time. Typically, conventional sensors can mitigate sensor drift by calibration, e.g., initially calibrating and re-calibrating the electrochemical sensor over a limited life span. Because sensor drift can be due to small and non-deterministic temporal variations of the sensor, it can plague the ability of the sensor to accurately measure non-pronounced events, e.g., such as a gradual change in temperature.

Biodegradation of sensor that lead to sensor drift can be observed as changes of current or voltage output signals, e.g., due to actual changes in resistance at the sensor electrodes. Biodegradation can also impact the membrane for facilitating the electrochemical reaction(s) for analyte detection by causing impedance to the permeability of analytes to reach the chemical reaction zone for the electrode signal generation consistency, and/or by increasing the impurity bio-products that can penetrate through the permeability membrane and result in the base electrode degradation. The example coating materials can enhance the stability and support the longevity of the performance duration of the sensor. For example, a bio-degradation inhibitor present in the coating enables the membrane to stay clear of bio-fouling and ensure the permeability of the membrane's matrix does not clog.

Figure 1C:
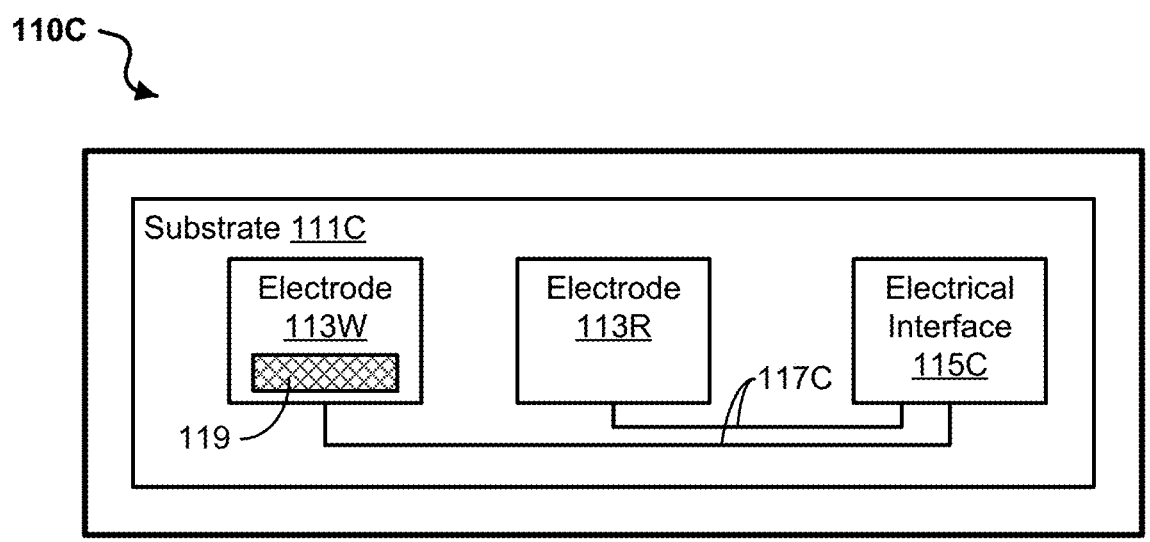
FIG. 1C shows a block diagram illustrating an example embodiment of a sensor unit for an analyte sensor, in accordance with the present technology.

FIG. 1C shows a block diagram illustrating an example embodiment of the sensor unit 110 for an analyte sensor, shown in FIG. 1C as sensor unit 110C. Similar to the example of the sensor unit 110B shown in FIG. 1B, the sensor unit 110C includes a wafer-based substrate 111C, a plurality of electrodes arranged on the substrate 111C, an electrical interface 115C comprising a plurality of electrical contact sites (e.g., pads, pins, etc.), and a plurality of interconnections 117C disposed on the substrate 111C and configured to couple the electrodes to respective contact sites of the electrical interface 115C. In some embodiments, the substrate 111C includes a wafer-based substrate, and in some embodiments, for example, at least some of the plurality of electrodes are configured as electrochemical sensor electrodes to detect an electrical signal corresponding to a reaction involving a target analyte in a fluid exposed to the electrodes. In some embodiments, for example, the plurality of electrodes are configured as a two-electrode sensor contingent, including at least one working electrode 113W and at least one reference electrode 113R, e.g., without a counter electrode associated with the sensor contingent. In other embodiments (not shown in FIG. 1C), for example, the plurality of electrodes are configured as a three-electrode sensor contingent, including at least one working electrode 113W, at least one reference electrode 113R, and at least one counter electrode (not shown). In various embodiments, for example, the at least one reference electrode 113R optionally includes iridium (e.g., iridium oxide). In various embodiments, for example, the at least one working electrode 113W optionally includes iridium and/or platinum (e.g., 90/10 platinum/iridium). In some embodiments, for example, the at least one working electrode 113W can be functionalized by the chemical layer 119 to interact with the target analyte to facilitate a reaction that results in a change in electrical charge potential and/or flow at or proximate the surface of the at least one working electrode 113W, such that an electrical signal associated with the reaction is detectable at the at least one working electrode 113W with respect to the at least one reference electrode 113R to measure a parameter associated with the target analyte. In some embodiments, the chemical layer 119 of the sensor unit 110C can include a membrane, such as the multi-layered membrane described in U.S. Patent Publication No. 2021/096157A1, titled "Chemically Fused Membrane for Analyte Sensing," which is incorporated herein by reference. Thus, in one embodiment the present disclosure provides a sensor device having an iridium electrode and a multi-layered membrane, optionally with other features as described herein. Example implementations of the sensor unit 110C may include any of the features and attributes of the sensor unit 110B, described above.

In one embodiment, the sensor device has a two-electrode contingent consisting of a working electrode and a reference electrode, optionally in sterile form. For clarity, a two-electrode contingent, or an electrode contingent consisting of two electrodes, has exactly two electrodes, not one electrode, not three electrodes, not more than three electrodes. In one embodiment the working electrode comprises a surface layer comprising glucose oxidase that is reactive with glucose present in a bodily fluid to which the two-electrode contingent is exposed. Underlying the layer of glucose oxidase is a layer of platinum, in one embodiment pure platinum, i.e., platinum composed of at least 95 weight % (wt %) platinum, or at least 96 wt %, or at least 97 wt %, or at least 98 wt %, or at least 99 wt % platinum based on the weight of metal that is present in this layer. In one embodiment, underlying the platinum layer is a titanium layer, in one embodiment formed from pure titanium, i.e., titanium composed of at least 95 weight % (wt %) titanium, or at least 96 wt %, or at least 97 wt %, or at least 98 wt %, or at least 99 wt % titanium metal based on the total metal that is present in this layer. Thus, in one embodiment the working electrode sits atop a silicon oxide substrate in a sandwich format, where the titanium layer is on top of and directly adjacent to the silicon oxide substrate, the platinum layer is on top of and directly adjacent to the titanium layer, and the glucose oxide-containing layer is on top of and is directly adjacent to platinum layer. In one embodiment the reference electrode comprises a surface layer comprising iridium oxide that is exposed to the fluid that contains glucose detected by the working electrode. Underlying the iridium oxide is a layer of iridium metal, operationally pure iridium metal, i.e., iridium composed of at least 95 weight % (wt %) iridium metal, or at least 96 wt %, or at least 97 wt %, or at least 98 wt %, or at least 99 wt % iridium metal based on the weight of metal that is present in this layer. Underlying the layer of iridium metal is a layer of platinum metal, optionally pure platinum metal, i.e., platinum composed of at least 95 weight % (wt %) platinum, or at least 96 wt %, or at least 97 wt %, or at least 98 wt %, or at least 99 wt % platinum based on the weight of metal that is present in this layer. Optionally this platinum layer is equivalent to, e.g., the same composition as, the platinum layer of the working electrode. Underlying the layer of platinum in the reference electrode is a layer of titanium, optionally pure titanium, i.e., titanium composed of at least 95 weight % (wt %) titanium, or at least 96 wt %, or at least 97 wt %, or at least 98 wt %, or at least 99 wt % titanium metal based on the total metal that is present in this layer. Optionally, the platinum layer in the reference electrode is equivalent to, e.g., the same composition as, the titanium layer that is also present in the working electrode. Thus, in one embodiment the reference electrode sits atop a silicon oxide substrate in a sandwich format, where the titanium layer is on top of and directly adjacent to the silicon oxide substrate, the platinum layer is on top of and directly adjacent to the titanium layer, the iridium metal layer is on top of and directly adjacent to the platinum metal layer, and the iridium oxide layer is on top of and directly adjacent to the iridium metal layer. The working electrode may be described as comprising, or consisting of, three layers: a titanium metal layer, a platinum metal layer, and a layer that comprises glucose oxidase. The reference electrode may be described as comprising, or consisting of, four layer: a titanium metal layer, a platinum metal layer, a iridium metal layer, and an iridium oxide layer. Optionally, the titanium metal layer of the working electrode is the same composition as the titanium metal layer of the reference electrode, and optionally the titanium metal layer of the working electrode is the same thickness as the titanium metal layer of the reference electrode. Optionally, the platinum metal layer of the working electrode is the same composition as the platinum metal layer of the reference electrode, and optionally the platinum metal layer of the working electrode is the same thickness as the platinum metal layer of the reference electrode.

Optionally, the surface area of the top surface of the reference electrode is greater than the surface area of the top surface of the working electrode. In one embodiment, the top surface of the working electrode has a shape selected from a circle and a square, in which case the top surface has a diameter (in the case of a circle) or a width (in the case of a square, where the width may also be referred to as the length), in addition to a central point. In one embodiment, the top surface of the reference electrode has a shape selected from a circle and a square, in which case the top surface has a diameter (in the case of a circle) or a width (in the case of a square, where the width may also be referred to as the length), in addition to a central point. For convenience, the diameter or width of the electrode will be referred to simply as the width, even though the electrode may have a circular shape.

The two-electrode contingent may be located on an electrically non-conductive substrate, e.g., silicon dioxide ($SiO_2$), where the non-conductive substrate may be in a wafer (planar) form as opposed to, e.g., a tubular form. Although in one embodiment the non-conductive substrate is present in a non-planar form.

In one embodiment, the working and reference electrode are located on a surface of the substrate, and are separated from one another by a distance. The distance is the separation between the center point of the reference electrode and the center point of the working electrode. In one embodiment, the distance between these two points is less than 4 times the width of the larger of the working electrode and the reference electrode, where in one embodiment the reference electrode has a greater width than the working electrode.

In one embodiment, the present disclosure provides a sensor device wherein the substrate is a wafer comprising silicon dioxide; the working electrode comprises a layer of titanium metal in direct contact with the substrate, a layer of platinum metal in direct contact with the layer of titanium metal, and a chemical layer in direct contact with the layer of platinum metal, the chemical layer comprising glucose oxidase configured to facilitate a reaction involving glucose that produces an electrical signal at the electrochemical sensor electrode contingent; and the reference electrode comprises a layer of titanium metal in direct contact with the substrate, a layer of platinum metal in direct contact with the layer of titanium metal, a layer of iridium metal in direct contact with the layer of titanium metal, and a layer of iridium oxide in direct contact with the layer of iridium metal. In embodiments, each of the mentioned titanium metal, platinum metal and iridium metal layers contains at least 95 wt % of the mentioned metal, or at least 96 wt % of the mentioned metal, or at least 97 wt % of the mentioned metal, or at least 98 wt % of the mentioned metal, or at least 99 wt % of the mentioned metal, each wt % value based on the total weight of the metal in the named layer. For example, in one embodiment, the titanium metal layer contains at least 99 wt % titanium metal, the platinum metal layer contains at least 99 wt % platinum metal, and the iridium metal layer contains at least 99 wt % iridium, based on the weight of the metal in each named layer.

In some implementations of the sensor unit 110C, for example, the sensor unit 110C can be integrated or incorporated into a wearable sensor device used in a sensor system, where sensor electrodes of the wearable sensor device is inserted into the body of a patient user. One example of a sensor system with which the sensor unit 110C can be integrated or incorporated includes embodiments of the transcutaneous analyte sensor system described in U.S. Pat. No. 8,615,282 B2, titled "Analyte Sensor," as incorporated herein. Another example of a sensor system with which the sensor unit 110C can be integrated or incorporated includes embodiments of the telemetered characteristic monitor system, including a percutaneous sensor set, described in U.S. Pat. No. 6,809,653 B1, titled "Telemetered Characteristic Monitor System and Method of Using the Same," which is incorporated herein by reference Another example of a sensor system with which the sensor unit 110C can be integrated or incorporated includes embodiments of the analyte monitoring system described in U.S. Pat. No. 7,920,907 B2, titled "Analyte Monitoring System and Method," which is incorporated herein by reference.

In one embodiment the sensor device of the present disclosure is sterile. Particularly when the sensor device is intended for in vivo placement, in one embodiment the sensor device is sterile. In one embodiment, at least the electrode contingent is sterile. When the electrode contingent contains an enzyme which should be a functioning enzyme, e.g., glucose oxidase when the electrode should assist in detecting and measuring the presence and/or concentration of glucose in a body fluid, the electrode contingent, and optionally also components associated with the electrode contingent, may be sterile. In one embodiment the sterilization is accomplished with e-beam sterilization. Optionally, the sterilization is accomplished using cold e-beam sterilization, i.e., e-beam sterilization performed on an electrode contingent at a cold temperature such as less than room temperature, e.g., less than 25° C., in order to maintain the activity of the immobilized enzyme.

Figure 2A:
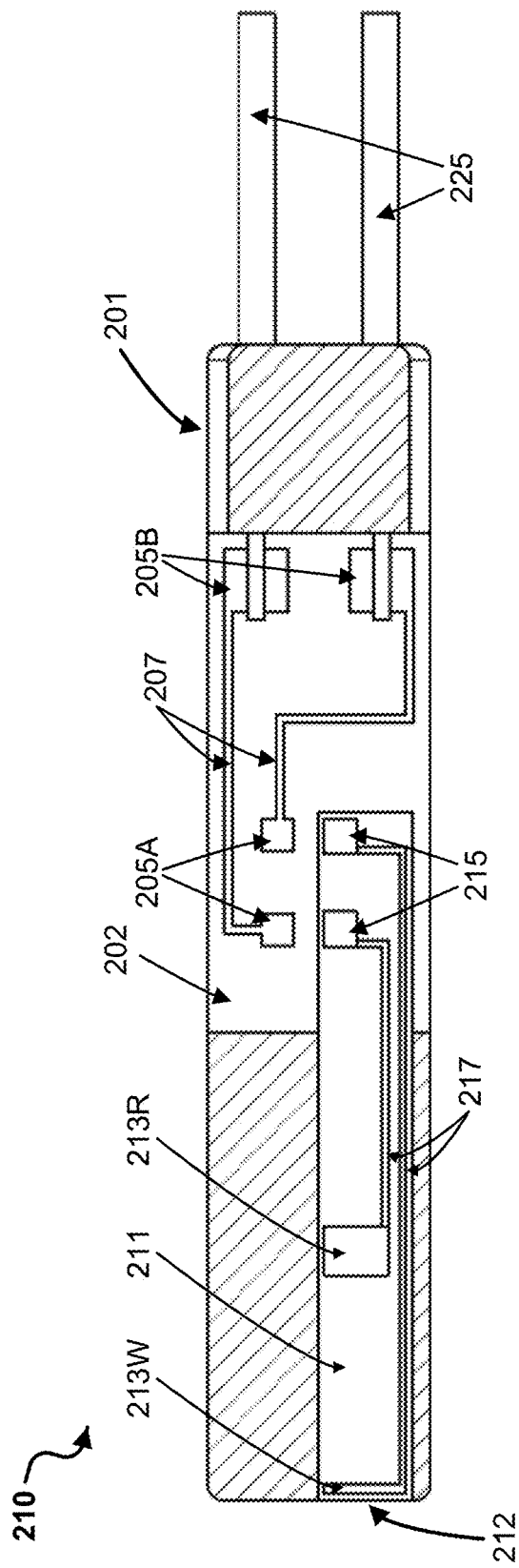
FIG. 2A shows a diagram depicting an example embodiment of a sensor unit for an analyte sensor device including a two-electrode sensor contingent, in accordance with the present technology.

FIG. 2A shows a diagram depicting a top view of an example embodiment of the sensor unit 110 of the analyte sensor device 100 having a two-electrode contingent, shown in FIG. 2A as sensor unit 210. The sensor unit 210 includes a sensor carrier system 201 and an electrochemical sensor electrode contingent 212 that can reversibly couple to and can electrically interface with the sensor carrier system 201. The sensor carrier system 201 is operable to electrically connect to the electronics unit 120 of the analyte sensor device 100 via electrical interface components 225 (e.g., wires, pins, or other electrically conductive structure). In some embodiments, for example, the electrical interface components 225 can span from the sensor unit 210 to contact electrically conductive contact sites of the electronics unit 120. Yet, in some embodiments (not shown), electrical interface components of the electronics unit 120 can span from the electronics unit 120 to contact electrically conductive contact sites of the sensor unit 210, e.g., within the sensor carrier system 201.

The electrochemical sensor electrode contingent 212 of the example sensor unit 210 shown in FIG. 2A includes a two-electrode contingent comprising a working electrode 213W and a reference electrode 213R, which are disposed on an electrically-insulative, wafer-based substrate 211 of the electrochemical sensor electrode contingent 212. In some embodiments of the sensor unit 210, for example, the working electrode 213W can include platinum, iridium, gold, silver, titanium, single- or multi-walled carbon nanotubes, and/or another electrically conductive material or a combination thereof. In some embodiments of the sensor unit 210, for example, the reference electrode 213R can include iridium (e.g., iridium oxide, or iridium/iridium oxide).

In example embodiments of the reference electrode 213R of the sensor unit 210 comprising iridium, the iridium-based reference electrode can provide longevity to the analyte sensor device 100 because the iridium oxide maintains a constant reference to balance the detectable signals; whereas silver oxide electrodes typically suffer damage over time by the voltage potentials (e.g., typically 300-350 mV) applied at the reference electrode, which limits their practical use for less than 30 days. In contrast, the example iridium oxide reference electrode allows the analyte sensor device 100 to operate at lower power (e.g., ~150 mV potential applied at the iridium-based reference electrode with an output current in a range of, for example, about 10 nA to 25 nA, as compared to measurements around and above 600 mV for conventional platinum electrodes, for example), thereby allowing sensor use for 1 year or beyond. Moreover, the iridium-based reference electrode can also enable the sensor system to function at a lower voltage potential, i.e., substantially less than 500 mV, for example, such as within a range of 100 mV to 200 mV; and thereby, due to operating at a lower potential difference across the working and (iridium-based) reference electrodes, prevent interference by secondary chemicals, such as dopamine, aspirin, acetaminophen, numbing chemicals used in medical treatments for pain, or others, which may also be present in the body environment being monitored by the in vivo or ex vivo sensor device of the present disclosure.

In example implementations, the two electrodes of the two-electrode contingent work in conjunction with each other to balance the measurable signal from noise in the biological system subject to detection by the sensor unit 210, e.g., whether intrinsic biological noise caused by cell or biomolecular interactions and processes or extrinsic noise caused by electronic systems internal or external to the patient user's body, such as peripheral electronic devices (cell phone, etc.) or other medical devices. For various example embodiments of the sensor unit 210, the electrochemical sensor electrode contingent 212 advantageously enables an sensor device 100 to have a substantially smaller footprint and be more reliable for signal processing, e.g., compared to some conventional electrochemical sensors with three or more electrodes.

The two-electrode sensor contingent can also provide enhanced gate control/response detection for stable or unstable environment aspects for signal processing. Furthermore, area/relationship factors can be critical for the operability of a two-electrode electrochemical sensor. For example, a specific area ratio of the working electrode area and reference electrode area is for the working electrode to have the smaller area and the reference electrode to have the larger area. The potential difference (e.g., the potential voltage between two similar or dissimilar electrode material surfaces) also factors into the electrode areas and affects a functional longevity to the overall signal performance. The present design of the example two-electrode contingent for various embodiments of the electrochemical sensor electrode contingent 212 enables a two-electrode design with example ratios of the smallest area (Working Electrode) to the largest area (Reference Electrode) including 1:15, or 1:10, or 1:5, or 1:4, or even smaller ratio based on the sensor longevity for the functional detection intended by the design. Example distances separating the working electrode 213W and the reference electrode 213R can be as small as 1 μm (one micron) or greater than a micron. For the example electrodes of the sensor unit 210 or other example embodiments of a sensor unit in accordance with the disclosed technology, the working electrode(s) and reference electrode(s) can be configured to have an area shown in Table 1. It is noted that the size, shape, and surface area configurations of the electrodes are not limited to those shown in Table 1.

TABLE 1

| Ratio (WE:RE) | Working Electrode (mm²) | Reference Electrode (mm²) |
| --- | --- | --- |
| 1:10 | 0.2 | 2.0 |
| 1:10 | 0.1 | 1.0 |
| 1:8 | 0.1 | 0.8 |
| 1:4 | 0.2 | 0.8 |
| 1:4 | 0.1 | 0.4 |
| 1:3 | 0.2 | 0.6 |
| 1:3 | 0.1 | 0.3 |
| 1:1 | 0.2 | 0.2 |

For example, the electrochemical sensor electrode contingent 212 having the two electrodes, the reference electrode 213R comprising iridium oxide and the working electrode 213W (e.g., comprising iridium), is operable to detect a parameter (e.g., concentration) of the target analyte (e.g., glucose, oxygen, etc.) while also detecting a change in an environmental condition (e.g., temperature) in the body region (zone) where the sensor unit 210 is deployed. The capability of the platinum working and iridium-based reference two-electrode contingent of the electrochemical sensor electrode contingent 212 to sense both changes in an analyte parameter (e.g., glucose concentration) and an environmental condition (e.g., temperature in the local environment of the sensor unit 210) is due, in part, to the immunity of electrode signal drift (i.e., stable iridium reference or counter electrodes' signal bias), such that pronounced signal changes detected across the working electrode 213W and reference electrode 213R are attributable to parameter changes associated with the target analyte, and subtle signal changes detected across the two-electrode contingent are attributable to a change in an environmental factor affecting the electrodes, such as a temperature increase. For example, the two-electrode electrochemical sensor electrode contingent 212, without a counter electrode, is configured to be sensitive to such changes in the environment, such as temperature, that cause a swing in the (otherwise stable) bias measurement to the analyte (e.g., glucose measurements). On the other hand, for a different configuration of the electrochemical sensor electrode contingent 212 having a three-electrode contingent, for example, a counter electrode would preclude the ability to measure the change in bias for the measured electrical signal between the working and reference electrodes that could otherwise be associated with such environmental changes, since a bias signal change is immediately adjusted for at the working electrode due to the counter electrode.

In some embodiments of the sensor unit 210, for example, the wafer-based substrate 211 includes silicon oxide (e.g., silica, glass, or other), germanium (e.g., undoped or doped), gallium arsenide, or other. The wafer-based substrate 211 can provide several advantages for the in vivo or ex vivo sensor device 100 in terms of operation, preparation, and/or fabrication. For example, the wafer-based substrate 211 can allow an end-user to modify the three-dimensional geometry of the electrodes and/or chemically modify (e.g., passivate) the substrate to facilitate conformance of the membrane used for electrochemical sensing, e.g., from a top-to-bottom approach. This enables the construction uniqueness of the sensor device from the point of surface build, as it pertains to material layer formation and electronics/communication integration from top to bottom on the substrate. This also enables fabrication of connections to processing components, e.g., allowing modifications in size and/or form, for specific mechanical and configuration construction. Importantly, for example, the wafer-based substrate 211 enables the ability to create a surface roughness on a sensor device to promote the enhancement of longevity of analyte sensing, e.g., where the surface roughness can (1) enable an RMS (root mean square) configuration that can be measured in a Peak-to-Peak or Peak-to-Valley manner and that increases the surface area in a 3D cross-sectional aspect, e.g., as compared to a 2D cross sectional aspect to enable a signal generating surface to be enlarged while maintaining the same perimeter for the chemical oxidase reaction. In some implementations of the disclosed analyte sensors, the wafer-based substrate may or may not maintain the initial base substrate material, e.g., silica, germanium, or other, such that the base substrate layer can act as a scaffolding of surface support as other material layers are compiled on the base substrate layer. In some examples, a polymer layer can be applied as a first layer on the base substrate, but which the polymer layer (first layer) is able to be lifted from the initial base layer, be it silica or other material layer(s), which can result in production of an electrode sensor with minimal stiffness when compared to the initial layer properties. For example, this aspect of the wafer-based substrate can result in a more connected and flexible layer based on the first polymer layer properties to enable more optimal handling and mechanical properties when delivered and implanted into the selected host position.

The electrochemical sensor electrode contingent 212 includes electrically conductive contact sites 215 and interconnection wires 217 disposed on or within the wafer-based substrate 211 and configured to couple the electrodes 213W, 213R to respective contact sites 215. In some embodiments of the sensor unit 210, for example, the electrically conductive contact sites 215 and/or the interconnection wires 217 can include platinum, gold, iridium, etc. In example implementations of the electrochemical sensor electrode contingent 212 on the wafer-based substrate 211, the substrate can be produced layer by layer and by mask/remask, as discussed above, which enables the overall sensor substrate to be built in (i) an interconnected layer by layer conjunction, or (ii) non-connected manner (as selected by design), such that only specific locations connect and communicate the signal from the electrodes to the electronics unit (e.g., control unit, signal processing circuit, and/or power source). This can enable more compact sizing and faster processing overall for the signal transfer.

In the example shown in FIG. 2A, the sensor carrier system 201 of the sensor unit 210 includes contact sites 205A connected to contact sites 205B via interconnections 207, each of which disposed on or in an electrically insulating substrate 202. The contact sites 205A are positioned on the substrate 202 so as to electrically interface with contact sites 215 of the electrochemical sensor electrode contingent 212; and the contact sites 205B are positioned on the substrate 202 to electrically interface with the electrical interface components 225, thereby electrically connecting the electrochemical sensor electrode contingent 212 with the electronics unit 120. It is noted that the top view diagram illustrates the contact sites 215 (of the electrochemical sensor electrode contingent 212) and the contact sites 205A (of the sensor carrier system 201) as spatially separated, which is done for illustrative purposes. It is understood that the contact sites 215 are disposed on an attachment side of the electrochemical sensor electrode contingent 212, and the contact sites 205A are disposed on the substrate 202 so as to align with the corresponding contact sites 215 when the electrochemical sensor electrode contingent 212 is coupled to the sensor carrier system 201 of the sensor unit 210. In various implementations, for example, certain components of the sensor unit 210 (e.g., contact sites 205, interconnections 207, substrate 202, etc.) are contained inside of the sensor carrier system 201 and protected from exposure to outside substances when the analyte sensor device 100 is deployed in vivo.

In some embodiments of the sensor unit 210, the working electrode 213W can include an embodiment of the chemical layer 119 for monitoring of a target analyte by the sensor unit 210. In some implementations, for example, the analyte sensor device 100 can be configured to detect glucose, oxygen, ketones, and/or other analytes, which can be measured by the sensor unit 210, where the electronics unit 120 transmits data representative of the detected electrical signals, which is then linked to the data processing system 150 (e.g., including uploading to the database 156) for analysis and continuous functional monitoring for evaluation of the subject's health status. For example, the data processing system 150 can apply the acquired analyte data (e.g., of glucose, oxygen, ketones, and/or other analytes) to baseline models for comparison, e.g., such as Clarke Error Grids or equivalent models, to base analysis and control methods associated with the user's health context and behaviors associated with food, vitamins, fluids, or prescribed medicines, or other. In some embodiments, for example, the analyte sensor device 100 is configured to detect electrical signal from the working and reference electrodes based on an engineered membrane (e.g., such as membrane 419, discussed later in FIG. 4) designed for analyte specificity directed to glucose, oxygen, and ketones.

In some embodiments of the sensor unit 210, for example, the sensor unit 210 includes additional interconnection electronic components that can facilitate interconnectivity and coupling of multiple electrochemical sensor electrode contingents to the sensor carrier system 201. An example embodiment of a multi-electrochemical sensor assembly for sensor unit 210 is shown later in FIG. 2C.

Figure 2B:
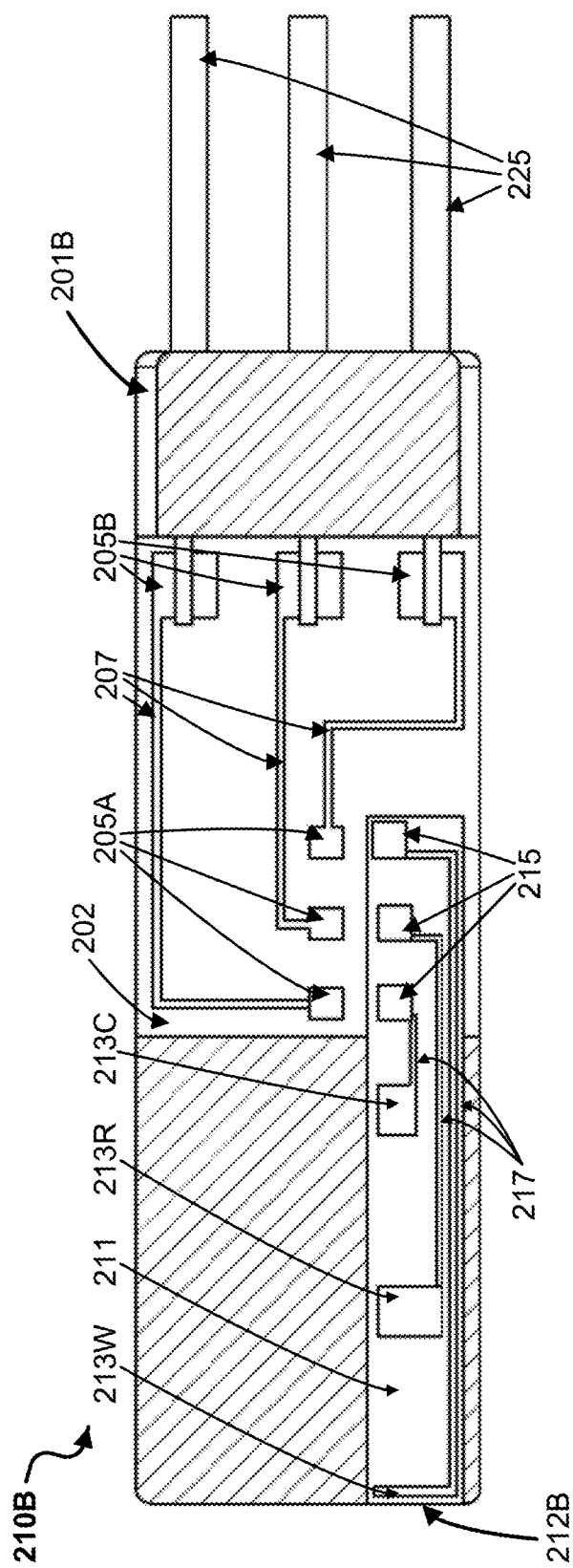
FIG. 2B shows a diagram depicting an example embodiment of a sensor unit for an analyte sensor device including a three-electrode sensor contingent, in accordance with the present technology.

FIG. 2B shows a diagram depicting a top view of an example embodiment of the sensor unit 110 of the analyte sensor device 100 having a three-electrode contingent disposed on an electrochemical sensor electrode contingent 212B, where the example embodiment of the sensor unit 110 shown in FIG. 2B is illustrated as sensor unit 210B. The electrochemical sensor electrode contingent 212B of the example sensor unit 210B shown in FIG. 2B includes a three-electrode contingent comprising an embodiment of the working electrode 213W, an embodiment of the reference electrode 213R, and a counter electrode 213C, which are disposed on an embodiment of the electrically-insulative, wafer-based substrate 211. In some implementations, for example, the counter electrode 213C can be used as a development tool and/or may be used to conjunct the reference signal balance to the working electrode, such as in a test mode for certain applications of the sensor unit 210B. There may be other instances with detection development that the counter electrode is preferred as a component of the electrochemical sensor electrode contingent. Also, for the illustrative diagram of FIG. 2B, as in FIG. 2A, it is understood that the contact sites 215 are disposed on an attachment side of the electrochemical sensor electrode contingent 212, and the contact sites 205A are disposed on the substrate 202 so as to align with the corresponding contact sites 215 when the electrochemical sensor electrode contingent 212B is coupled to the sensor carrier system 201B of the sensor unit 210B.

Figure 2C:
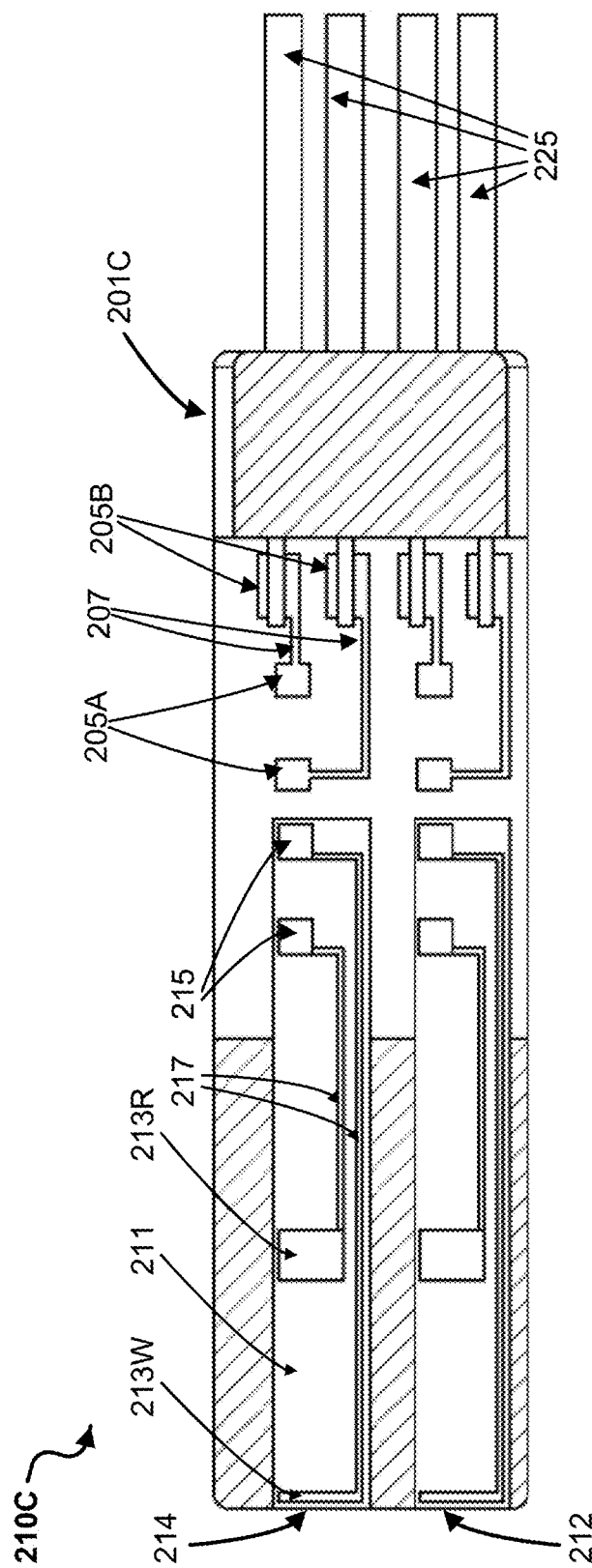
FIG. 2C shows a diagram depicting an example embodiment of a sensor unit for an analyte sensor device including multiple two-electrode sensor contingents, in accordance with the present technology.

FIG. 2C shows a diagram depicting a top view of an example embodiment of the sensor unit 110 of the analyte sensor device 100 having multiple two-electrode contingents, shown in FIG. 2C as sensor unit 210C. In such embodiments, for example, the sensor unit 210C includes a plurality of sets of the contact sites 205A, the contact sites 205B and the interconnections 207 to electrically interface with a plurality of electrochemical sensor electrode contingents, e.g., the electrochemical sensor electrode contingent 212 and a second electrical sensor electrode contingent 214 shown in the example of FIG. 2C. In this example, the second electrochemical sensor electrode contingent 214 is configured to have the same or similar structure as the electrochemical sensor electrode contingent 212; yet, in some embodiments, the working electrode 213W of the second electrochemical sensor electrode contingent 214 may be modified with a different chemical layer 119 than the chemical layer 119 on the working electrode 213W of the electrochemical sensor electrode contingent 212 to sense a different target analyte when the sensor 210C is deployed and operated in vivo. In some embodiments, for example, the plurality of electrochemical sensor electrode contingents can share a same substrate; whereas in some example embodiments like that shown in FIG. 2C, the plurality of electrochemical sensor electrode contingents can be configured on separate substrates. Also for the illustrative diagram of FIG. 2C, as in FIG. 2A, it is understood that the contact sites 215 are disposed on an attachment side of the electrochemical sensor electrode contingent 212 and the second electrochemical sensor electrode contingent 214, and the contact sites 205A are disposed on the substrate 202 so as to align with the corresponding contact sites 215 when the electrochemical sensor electrode contingent 212 and the second electrochemical sensor electrode contingent 214 are coupled to the sensor carrier system 201C of the sensor unit 210C.

Figure 3:
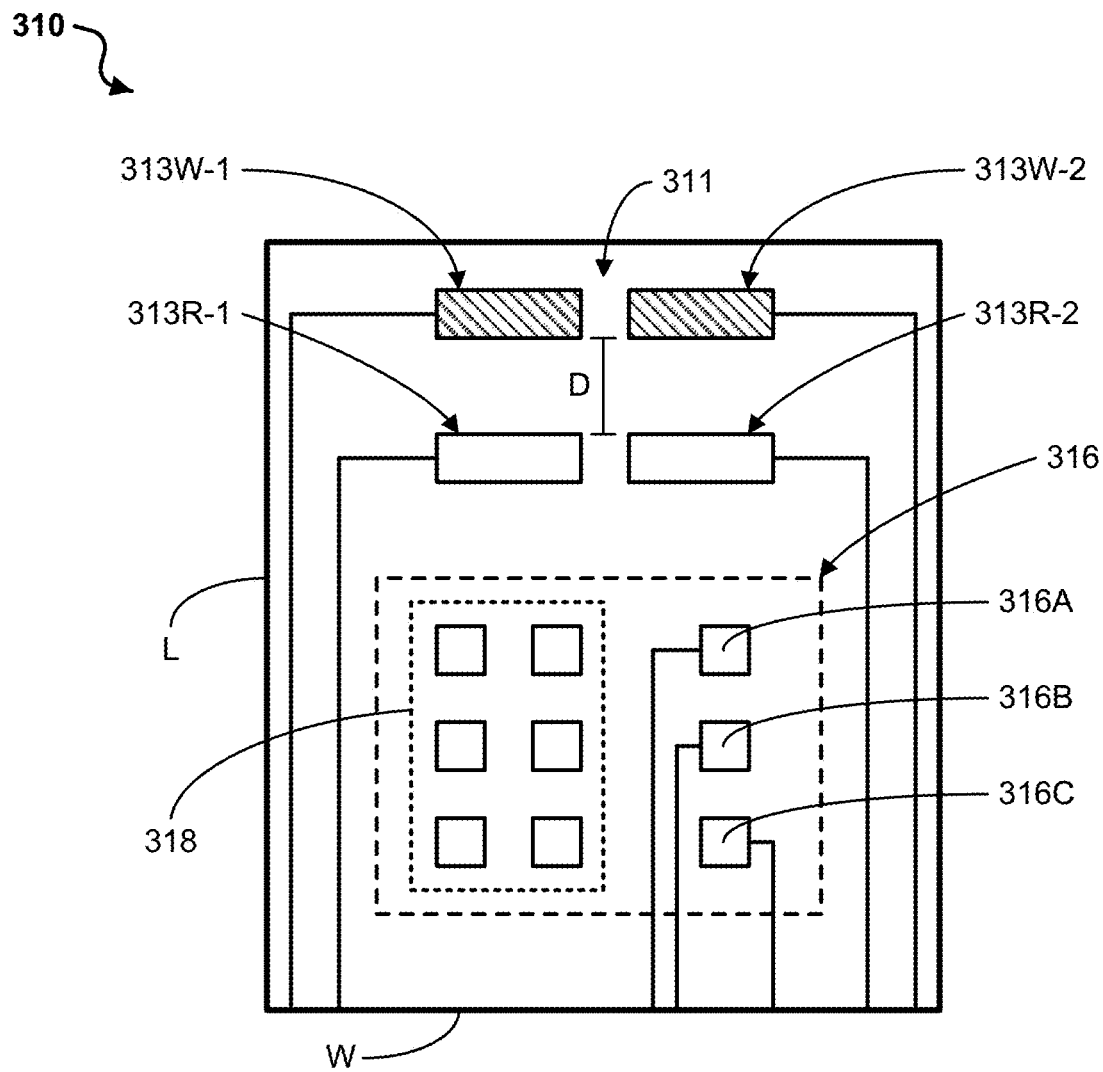
FIG. 3 shows a diagram of another example embodiment of the sensor unit for an analyte sensor device, in accordance with the present technology.

FIG. 3 shows a diagram of another example embodiment of the sensor unit 110 of the analyte sensor device 100 having a two-electrode electrochemical sensor electrode contingent and an electrical conductivity sensor, shown in FIG. 3 as sensor unit 310. The sensor unit 310 includes at least one two-electrode contingent disposed on an electrically-insulative, wafer-based substrate 311. In the example shown in FIG. 3, the sensor unit 310 includes a first electrode contingent comprising a first working electrode 313W-1 and a first reference electrode 313R-1, and a second electrode contingent comprising a second working electrode 313W-2 and a second reference electrode 313R-2. The wafer-based substrate 311 can be configured of a certain size, such that multiple sensor units 310 can be fabricated on a single wafer. In some embodiments of the sensor unit 310, for example, the working electrodes 313W and the reference electrodes 313R can include the materials as described for the embodiments of the electrodes 113W and 113R, the electrodes 213W and 213R, or other embodiments of working and reference electrodes, as discussed herein. For example, the working electrodes 313W can include platinum, iridium, and/or a combination thereof (e.g., such as 90% platinum/10% iridium working electrode); and the reference electrodes 313R can include iridium (e.g., iridium oxide).

In some embodiments of the sensor unit 310, the wafer-based substrate 311 includes 1 mm×1.5 mm area for a side W and a side L, respectively. In this and other example embodiments of the sensor unit 310, the first working electrode 313W-1 and the second working electrode 313W-2 are each spaced apart to a distance D with respect to the first reference electrode 313R-1 and the second reference electrode 313R-2, respectively. Example distances separating the working electrode(s) 313W and reference electrode(s) 313R can be as small as 1 μm (one micron) or greater than a micron. Similarly, for example, the first working electrode 313W-1 and the second working electrode 313W-2 can be spaced apart a certain distance, e.g., to ensure a non-cross communication action occurs, i.e., non-interference of signals from another electrode or electrodes. Additionally, or alternatively, the first working electrode 313W-1 and the second working electrode 313W-2 can be built around an insulator structure so as to ensure the two electrodes do not act as one electrode.

The distance or gap between the multiple working electrodes 313W-1 and 313W-2 can be as small as a micron or greater than a micron, e.g., depending on the desired form and fit configuration for the intended use of the sensor unit 310 when delivered and placed in the host. Similarly, for example, the distance or gap between the multiple reference electrodes 313R-1 and 313R-2 can be as small as a micron or greater than a micron. In this and other example embodiments of the sensor unit 310, the working electrodes 313W and reference electrodes 313R can be configured to have an area, as shown previously in Table 1.

For an electrode contingent, the reference electrode 313R is able to provide a complement balancer for the signal, which can enable reduction or elimination of signal noise in the signal processing (e.g., signal-to-noise analysis) by the signal conditioning unit 123 and/or data processing unit 121 of the electronics unit 120. In some embodiments of the sensor unit 310, for example, the working electrode 313W includes a membrane (e.g., such as membrane 419, discussed later in FIG. 4) designed for analyte specificity directed to the target analyte, e.g., glucose, oxygen, a ketone, or other. The working electrode 313W serves as the primary reaction site for an electrochemical reaction generating signal, which, among other things, can confirm that the sensor is detecting fluid containing oxygen and/or glucose or ketones, based on the configuration of the working electrode by its chemical layer 119, e.g., such as the membrane permeability and catalytic or reactive material of the layer. In example implementations using $IrO_2$ electrodes, the iridium oxide provides longevity for the sensor unit 310, as the electrodes do not deteriorate or stop functioning during electrochemical sensing operations; the iridium oxide effectively allows a self-populating electrochemical reaction (albeit, that is not endless), which enables the reference electrode to maintain function in conjunction with the working electrode.

Based on the two-electrode contingent design, materials, and spacing of the working and reference electrodes 313W and 313R, the sensor unit 310 is able to have a reduced size and enable lower potential voltages for detecting the target analyte(s) at the electrodes, which thereby provides the sensor unit 310 with the capability to function longer and with greater stability.

The sensor unit 310 includes an electrical conductivity sensor 316 comprising one or more electrodes (e.g., electrodes 316A, 316B, and 316C in the example shown in FIG. 3) that the sensor unit 310 can use to determine a presence of a fluid and/or a fluid property, e.g., fluid transmission or conductivity property (e.g., fluid flow rate, pressure, and/or viscosity), osmolarity and/or osmolality. In some implementations, for example, the electrical conductivity sensor 316 can determine the presence of a fluid upon the sensor unit 310 by determining a change in electrical signal (e.g., voltage or current) across at least any two electrodes of the electrodes of the electrical conductivity sensor 316, e.g., at least two electrodes of the electrodes 316A, 316B, and 316C in the example shown in FIG. 3. In this manner, for example, the electrical conductivity sensor 316 can provide the sensor unit 310 with a gated switch, e.g., by monitoring a minimum of two electrodes of the electrical conductivity sensor 316, where the output signal can be used as an indicative signal of a fluid property (e.g., sufficient moisture on the sensor) and/or as a control signal for operating other components of the sensor unit 310 (e.g., an ON/OFF switch to apply a voltage for operation of a two-electrode electrochemical sensor electrode contingent 313.

For example, in such implementations of the sensor unit 310, one or more of the electrodes 316A, 316B, and/or 316C can be excited (electrically stimulated) to detect parameters associated with the body fluid exposed to the sensor unit 310 to ensure the detected signals are being detected in a fluid rich environment. For example, when a body fluid decreases, the signal detected via the one or more electrodes 316A, 316B, and/or 316C decreases to a negligible level;

such implementations can provide a second identifier for fluid transmission in parallel with the analyte measurements detectable by the electrochemical sensor electrode contingent.

As an illustrative example, in certain implementations where an analyte sensor device 100 comprising the sensor unit 310 is deployed in the body, the in vivo analyte sensor device 100 may reside in a portion of the body that forms an interstitial cavity (or "pocket"). In such situations, the electrical conductivity sensor 316 of the sensor unit 310 can detect signals associated with fluid transmission that can provide an indication of isolation of the sensor from the body fluid (sometimes referred to as "pocket healing"), which can be due to scar tissue formation or other, where the deployment site is potentially inadequate for desired analyte and environmental conditions sensing. In some implementations, characterizing "pocket healing" at the sensor deployment site can be indicative of the need for replacement or new site selection. This can be important for certain types of implantable devices (to which the in vivo analyte sensor device 100 is attachable), where indication of "pocket healing" can be indicative of a desired or undesired outcome associated with the implantable device.

As an example of "pocket healing" detection, if the sensor unit 310 is in a moist environment and adequate lubricity is present, the electrical conductivity sensor 316 (operable as a switch sensor) should connect; and if the sensor unit 310 is not in a moist environment with adequate lubricity, then the electrical conductivity sensor 316 will not connect and such non-connection will be an indicator for such things as a "dry" interstitial pocket. In another example, if an in vivo analyte sensor device 100 comprising the sensor unit 310 is deployed in an aneurism, the electrical conductivity sensor 316 of the sensor unit 310 can be implemented to provide a second identifier for fluid transmission from the artery through the aneurysm neck and into the aneurysm body or sac.

In some embodiments of the sensor unit 310, for example, the electrodes of the electrical conductivity sensor 316 can used as a conductive switch system, like in the examples discussed above; whereas in some embodiments, for example, the electrodes of the electrical conductivity sensor 316 can additionally or alternatively be used as additional electrochemical sensor electrodes for the electrochemical sensor electrode contingent 313, e.g., such as a counter electrode or as additional working or reference electrodes. For example, as additional working and/or reference electrodes, utilization of electrodes from the electrical conductivity sensor 316 can be used to modify (e.g., optimize) the performance of the electrochemical sensor electrode contingent 313 based on modification of a desired ratio for functional working-to-reference electrodes.

In some implementations, for example, the sensor unit 310 is able to detect a degree of hydration of a biofluid on the sensor unit 310, e.g., particularly hydration of the membrane over the electrode(s), based on the potential charge at the electrical conductivity sensor 316. For such implementations, for example, the sensor unit 310 is operable to provide a quick equilibration/calibration protocol for the example analyte sensor device 100, e.g., such as 30 minutes or less, where the electrodes 316A, 316B, etc. are pre-exposed through a cascading voltage cycle prior to sensor implementation. The example equilibrium/calibration protocol can improve stability for specific hydration levels in the covering membrane, which can enable the membrane to quickly react with the biofluid when the analyte sensor device 100 is inserted into the sensing location of the patient user. A potential static charge may be applied at the electrode(s) 316A, 316B, 316C (or a second parallel electrode array 318) for enabling the charge to release once moisture is about the sensor membrane and the membrane swells to enable the chemical reaction to occur, e.g., which can enhance the hydration mechanism and shorten the initiation period for the sensor function.

Figure 4:
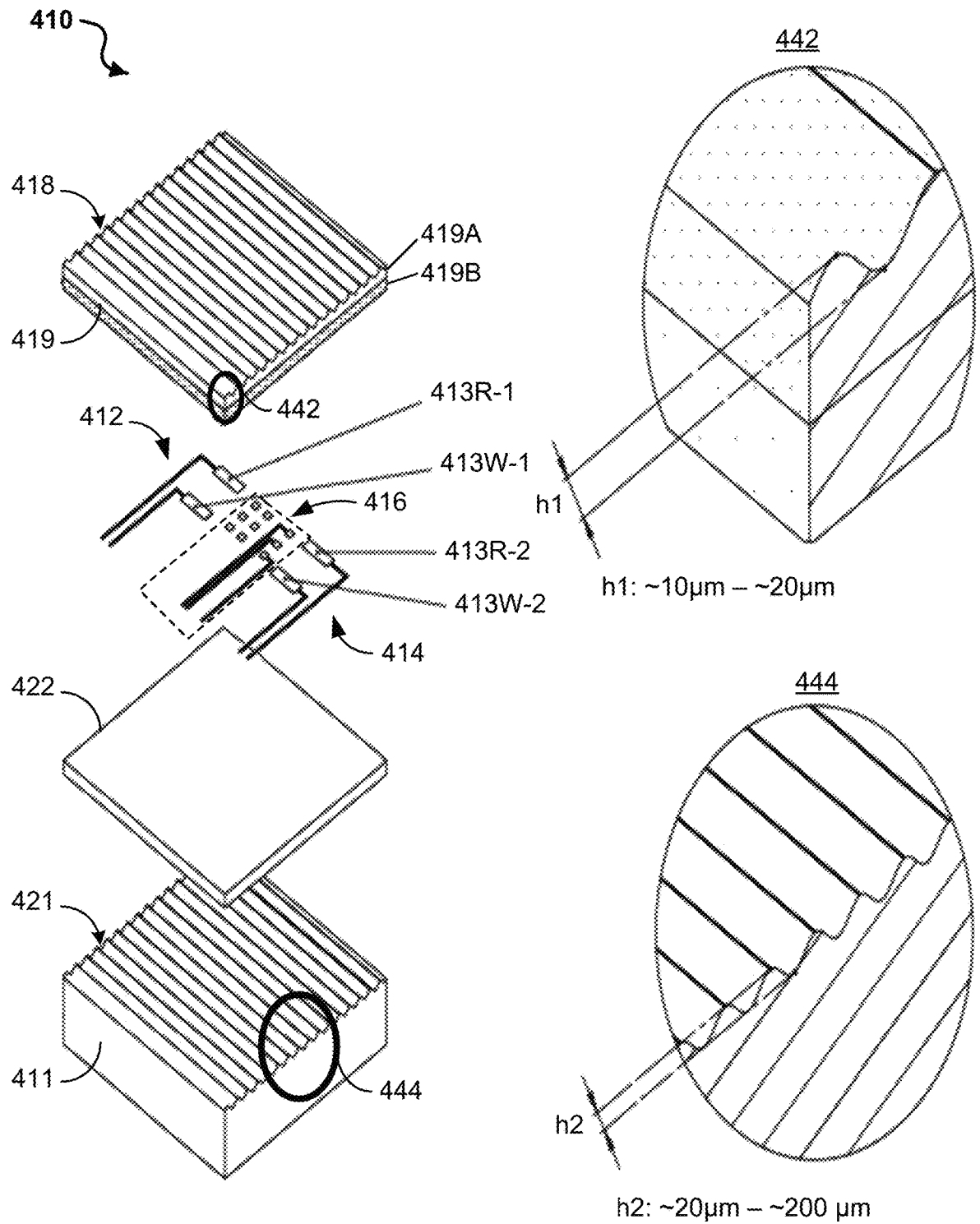
FIG. 4 shows a diagram of another example embodiment of the sensor unit for an analyte sensor device, in accordance with the present technology.

FIG. 4 shows a diagram illustrating an exploded view of another example embodiment of the sensor unit 110 of the analyte sensor device 100 having a plurality of two-electrode electrochemical sensor electrode contingents and multi-electrode conductivity sensor assembly, shown in FIG. 4 as sensor unit 410. The sensor unit 410 includes a first two-electrode electrochemical sensor electrode contingent 412 and a second two-electrode electrochemical sensor electrode contingent 414, each disposed on an electrically-insulative, wafer-based substrate 411. In this example, the first electrochemical sensor electrode contingent 412 includes a first working electrode 413W-1 and a first reference electrode 413R-1, and a second electrochemical sensor electrode contingent 414 includes a second working electrode 413W-2 and a second reference electrode 413R-2. The sensor unit 410 can include an electrode pad region 416, e.g., to provide an electrical conductivity sensor switch for the sensor unit 410. In some implementations, the electrode pad region 416 is configured as the electrical conductivity sensor 316 of the sensor unit 310 shown in FIG. 3. Additionally or alternatively, for example, the electrode pad region 416 can be configured to provide a second set of sensor electrode(s) for the two-electrode electrochemical sensor electrode contingents. In some implementations, at least two electrodes of the electrode pad region 416 can act as a switch to enable signal transmission to the processing unit of the electronics unit 120 in communication with the sensor unit 410, e.g., which can confirm the electrodes are 'on' for electrochemical sensing applications.

The sensor unit 410 includes a multi-layered membrane 419 coupled to at least the working electrodes 413W-1 and 413W-2 of the electrochemical sensor electrode contingents 412 and 414, respectively. The membrane 419 is structured to include an outer layer 419A that regulates permeation of reactive species and an inner layer 419B coupled to the outer layer and attachable to the electrochemical sensor electrode contingents 412 and 414 that immobilize a catalyst (e.g., GOx for certain applications of glucose sensing) to facilitate a reaction by the permeated reactive species for detection of the target analyte in a biofluid exposed to the sensor unit 410, when deployed in vivo. The membrane 419 can be configured to have various size thicknesses, which can be tailored for the desired application of the sensor unit 410. For example, in some embodiments, the membrane 419 can have a thickness of 10 µm or less or of 5 µm to 10 µm.

In some embodiments, for example, the membrane 419 can include a plurality of ripples 418 of the outer layer 419A that present a three-dimensional profile of the membrane 419. For example, the plurality of ripples 418 are configured to promote functional longevity of electrochemical sensor electrode contingent(s), e.g., the first two-electrode electrochemical sensor electrode contingent 412 and the second two-electrode electrochemical sensor electrode contingent 414, by facilitating increased signal stability of the detected electrical signal and preventing fouling of the electrodes, e.g., particularly the working electrode. In some embodiments of the membrane 419 having the plurality of ripples 418, the plurality of ripples 418 can be configured to have a height (h1) a range of 10 µm to 20 µm. In some embodiments, for example, the spacing (peak-to-peak) between ripples of the plurality of ripples of the membrane 419 includes 500 nm or greater, e.g., such as 500 nm to 5 µm.

In some embodiments, like the example shown in FIG. 4, the electrically-insulative, wafer-based substrate 411 of the sensor unit 410 includes a ridged surface 421 that is structured to include a plurality of peaks and valleys on the top surface of the substrate 411. The peaks and valleys of the ridged surface 421 can be configured uniformly (e.g., periodically) or nonuniformly (e.g., periodically). The electrochemical sensor electrode contingent(s) and multi-electrode conductivity sensor assembly(ies) couple to the wafer-based substrate 411, so as to take on the geometry of the ridged surface 421. In some optional embodiments, for example, the sensor unit 410 includes a flexible material layer 422 (e.g., polyimide) that couples between the sensor contingents and/or assemblies and the ridged surface 421 of the wafer-based substrate 411.

In FIG. 4, a cut-away insert 442 is shown depicting ripples 418 of the top surface of the example membrane 419. In this example, the ripples 418 of the membrane 419 include an example height (h1) from peak to valley in a range of about 10 µm to 20 µm. In example embodiments of the membrane 419, the height of the rides from peak to valley can include a range of about 5 µm to 50 µm. FIG. 4 also shows a cut-away insert 444 depicting an enlarged view of the peaks and valleys of the ridged surface 421 of the substrate 411, e.g., which illustrates an example height (h2) from peak to valley of the ridged surface 421 in a range of about 20 µm to about 200 µm. In some embodiments, for example, the spacing (peak-to-peak) between ridges of the ridged surface 421 of the substrate 411 includes 1 µm or greater, e.g., such as 1 µm to 5 µm.

The sensor unit 410 is designed to provide a surface profile, for example, which in some embodiments include the ripples 418 from the top surface of the membrane 419 and/or the ridges 421 of the substrate 411 to promote the functional longevity of sensor unit 410 in the analyte sensor device 100 when deployed in a subject's body. This three-dimensional surface profile is able to increase surface area of the membrane 419 while remaining in the same minimal-sized footprint of the sensor contingents 412, 414 on the wafer-based substrate 411, e.g., thus enabling signal consistency and longevity of reaction without surface fouling during use to generate the detectable signals associated with the target analyte. For example, the peak-to-valley surface profile of the membrane 419, e.g., which can be produced based on the initial profile of the ridged surface 421 of the substrate 411, can inhibit cell endothelization on the sensor, which could otherwise act as a coating on the membrane that impedes or blocks the interaction of the membrane 419 with the biofluid in contact with the sensor, and thus impedes analyte sensing. Furthermore, the three-dimensional (e.g., rippled and ridged) surface profile of the sensor unit 410 is able to act as a "used layer" or oxide covering, while allowing additional reaction and surface exposure to the chemistry. For example, the three-dimensional profile of the sensor unit 410 provides the sensor unit 410 with permeability function to allow transport of the desired reactive species that supports the electrochemical sensing of the target analyte, while over time degrading to a level that does not affect the permeability or function of the membrane. The composition and structure of the membrane 419 is configured for management of the signal detection, e.g., based on the membrane stoichiometry and viscosity, which can be varied for specific sensing applications in specific areas of the patient's body where the analyte sensor device 100 is to be deployed. In some implementations, a specified area of the sensor unit 410 for coating by the membrane 419 may be controlled by a material application process, including a micro/angstrom-liter drop process or a drop spin coat process.

As shown in insert 442 of FIG. 4, the height (h1) of the ripples 418 of the membrane 419 can be about 20 µm from peak to valley. This height of the ripples 418 of the membrane 419 can allow for the sensor unit 410 to maintain the point of measure (peak to valley) from the contact surface on the working electrode 413 to the top of the membrane 419 above that surface. In some embodiments, the height of the ripples 418 of the membrane 419 is no greater than 10 µm from peak to valley, e.g., which enhances membrane permeability and function for the detection of glucose, oxygen, and other analytes.

In some embodiments of the sensor unit 410, for example, the ripples 418 of the membrane 419 are created based on the coating fabrication on the ridged surface 421 of the wafer-based substrate 411, i.e., the rippled surface of the membrane 419 can take on the ridged profile of the sensor unit 410 (e.g., sensor contingents 412, 414, electrode pad region 416, substrate 411) based on the fabricated ridged surface 421 of the substrate 411. Additionally or alternatively, in some embodiments of the sensor unit 410, for example, the ripples 418 of the membrane 419 are created on the outer surface 418 of the membrane 419.

In some example implementations, the one or more analyte sensor devices 100 can be coupled to an implant device such as a total knee replacement (TKR) device, a stent, a pacemaker, or other implantable device. For some implementations where the implant device includes a power supply, for example, the analyte sensor device 100 can be integrated with the implant device to utilize power supplied by the implant device. Whereas in some example implementations, the one or more analyte sensor devices 100 can be placed independently within the patient user's body (e.g., not attached to other implant device or structure), where the entire an in vivo analyte sensor device 100 is completely inserted under the skin of the user (e.g., below the hair follicle for exposure to interstitial fluid or blood) that enables hydration of a functionalization layer to facilitate reaction of the target analyte and of the sensor electrodes, such that the in vivo analyte sensor device 100 can be operational within two hours of insertion.

Figure 5:
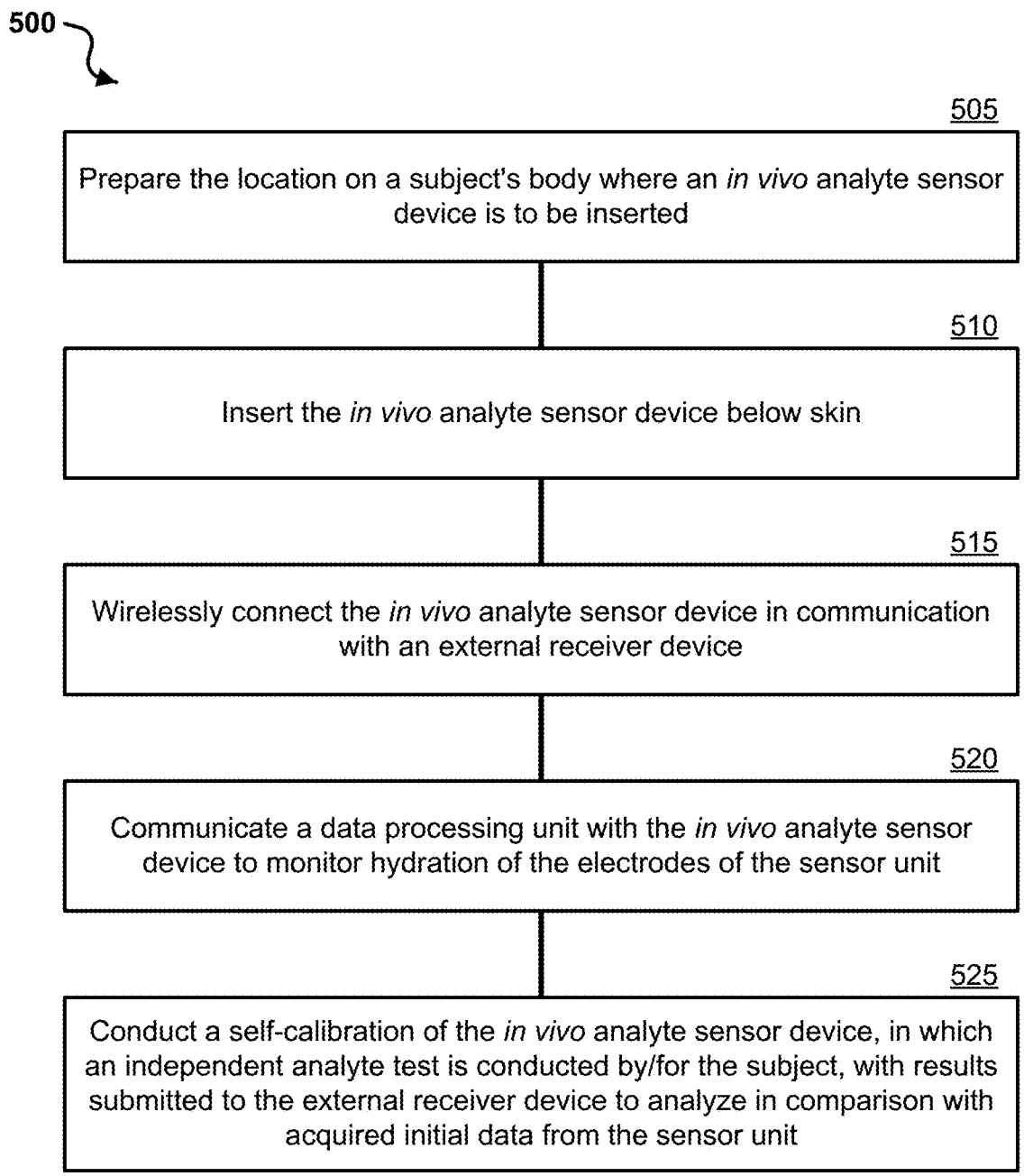
FIG. 5 shows a diagram illustrating a method 500 for deploying and activating an independent analyte sensor device 100 in a subject, in accordance with the present technology.

FIG. 5 shows a diagram illustrating a method 500 for deploying and activating an independent in vivo analyte sensor device 100 in a subject, in accordance with the present technology. The method 500 includes a process 505 to prepare the location on the subject's body where the in vivo analyte sensor device 100 is to be inserted, e.g., which can include shaving the skin and wiping the skin with a disinfectant solution, such as alcohol, iodine, etc. The method 500 includes a process 510 to insert the in vivo analyte sensor device 100 below skin. In implementations of the process 510, the sensor placement is selected for protection from undesired or external fluid and/or temperature interference. The method 500 includes a process 515 to wirelessly connect the in vivo analyte sensor device 100 in communication with the receiver device 130. The method 500 includes a process 520 to communicate a data processing unit (e.g., resident on the receiver device 130, a client computer device 154 of the data processing system 150, and/or a remote computing device 160) with the electronics unit 120 of the in vivo analyte sensor device 100 to monitor hydration of the electrodes of the sensor unit 110. The method 500 includes a process 525 to conduct a self-calibration of the in vivo analyte sensor device 100, in which an independent analyte test is conducted by/for the subject, with results submitted to the receiver device 130 and/or the data processing system 150 to analyze in comparison with acquired initial data from the sensor unit 110. In example implementations, the process 525 calibrates the in vivo analyte sensor device 100 to verify sensor function and monitoring functions of the app operating on the receiver device 130 and/or the client computer device 154 of the data processing system 150. Upon implementation of the method 500, the in vivo analyte sensor device 100 is able to function for intended use and duration in sensing the primary analytes (e.g., glucose and/or oxygen and/or ketones) and secondary analytes or physiological factors, e.g., including but not limited to temperature, vibration, water, or other at the deployment site of the in vivo analyte sensor device 100. In some implementations, the method 500 can be repeated for a new sensor after the in vivo analyte sensor device 100 has expired, which can be 90 days or beyond, including 1 year or beyond, for certain example embodiments of the in vivo analyte sensor device 100.

In additional embodiments, the present disclosure provides methods of detecting the presence of, and optionally measuring the amount of, an analyte in a biological fluid. For example, the present disclosure provides: (1) A method for in vivo detecting the presence of an analyte in a biological fluid, the method comprising implanting inside a patient a sensor device as described herein, e.g., a sensor device of any of the device embodiments identified herein, exposing the sensor device to the biological fluid inside the patient, generating an electric signal by the sensor device that is responsive to the presence of the analyte in the biological fluid, and converting the electric signal to an observable indication of the presence of the analyte in the biological fluid, where optionally the sensor device may capture, display and/or transmit data associated with the electrical signal; and (2) A method for ex vivo detecting the presence of an analyte in a biological fluid, the method comprising locating on a surface of a patient a sensor device as described herein, e.g., a sensor device of any of the device embodiments as identified herein, exposing the sensor device to the biological fluid on the surface of the patient, generating an electric signal by the sensor device that is responsive to the presence of the analyte in the biological fluid, and converting the electric signal to an observable indication of the presence of the analyte in the biological fluid, where optionally the sensor device may capture, display and/or transmit data associated with the electrical signal; and (3) A method for ex vivo detecting the presence of an analyte in a biological fluid, the method comprising locating on a medical device that includes a biological fluid conduit, e.g., a catheter, a sensor device of any of the device embodiments as identified herein, exposing the sensor device to the biological fluid contained within the biological fluid conduit, generating an electric signal by the sensor device that is responsive to the presence of the analyte in the biological fluid, and converting the electric signal to an observable indication of the presence of the analyte in the biological fluid, where optionally the sensor device may capture, display and/or transmit data associated with the electrical signal; and (4) A method for in vitro detecting the presence of an analyte in a biological fluid, the method comprising locating a sensor device as described herein, e.g., a sensor device of any of the device embodiments as identified herein, at an in vitro location, exposing the sensor device to the biological fluid at the in vitro location, generating an electric signal by the sensor device that is responsive to the presence of the analyte in the biological fluid, and converting the electric signal to an observable indication of the presence of the analyte in the biological fluid, where optionally the sensor device may capture, display and/or transmit data associated with the electrical signal.

The biological fluid may be a fluid that is present within a host, or the biological fluid may be a fluid that has exited the host, e.g., blood that has exited the host due to a blood draw, or has exited the host through a catheter or other biological fluid conduit that is connected to the host, or has exited the host due to trauma, e.g., bleeding due to a cut of the host. A biological fluid may thus refer to fluid present in a host as well as fluid that has exited a host and may optionally be in modified form, e.g., is in concentrated form due to evaporation of water from the biological fluid. The sensor may be implanted within the host, in which case in vivo biological fluid will be monitored. The sensor may be located entirely on a surface of the host, or in a medical apparatus such as a catheter or other conduit coupled to a host that can carry fluid from the host, in which case ex vivo biological fluid will be monitored. The sensor may be placed in an in vitro location, such as a laboratory apparatus not physically connected to the host, in which case in vitro biological fluid will be monitored. In one embodiment, the analyte is glucose and the sensor detects the presence of glucose in the biological fluid. In one embodiment, the analyte is glucose and the sensor detects and obtains data that is reflective of the amount of glucose in the biological fluid. In one embodiment the biological fluid is blood.

The sensor device is exposed to the biological fluid, or in other words the biological fluid comes into contact with the sensor device. Such exposure or contact includes the situation where the sensor device is in continuous contact with the biological fluid and is periodically monitoring for the present of analyte. Upon sensing the analyte, the sensor device will respond by generating an electric signal, where the properties of the electrical signal may also indicate the amount or concentration of analyte in the biological fluid. That electric signal may be converted into an observable indication of the presence and/or amount of analyte in the biological fluid. For example, the observable indication may be a display that is a component of the sensor device, where the display may show a number indicative of the amount of analyte being detected by the sensor device. As another example, the electric signal may be transmitted, either wirelessly or via a wired connection, to a separate device, e.g., a laptop or a smartphone, where the separate device creates an observable indication of the presence and/or amount of the analyte. Optionally, the electric signal may cause data to be stored in a memory, e.g., a memory chip, of the sensor device, where that data reflects and presence and/or amount of analyte in the sample fluid, and the data is stored until it is converted to an observable indication of the presence and/or amount of analyte in the sample, i.e., of detection of the analyte in the sample.

Examples

In some embodiments in accordance with the present technology (example A1), a sensor device for in vivo or ex vivo monitoring of analytes includes a substrate comprising an electrically non-conductive material; an electrochemical sensor electrode contingent disposed on the substrate and configured to detect a target analyte in a body fluid when the electrochemical sensor electrode contingent is deployed fully within a subject's body, the electrochemical sensor electrode contingent comprising, or optionally consisting of, a working electrode and a reference electrode associated with the working electrode, wherein the working electrode is functionalized by a chemical layer configured to facilitate a reaction involving the target analyte that produces an electrical signal at the electrochemical sensor electrode contingent; and an electronics unit in communication with the electrochemical sensor electrode contingent, the electronics unit comprising a wireless communications unit including a wireless transmitter or wireless transceiver to transmit data associated with the electrical signal to an external processor.

Example A2 includes the sensor device of any of examples A1-A45, wherein, the processor is operable to determine a parameter associated with the target analyte based on the electrical signal measured at the electrochemical sensor electrode contingent, and wherein the processor is configured to determine from the same electrical signal produced at the electrochemical sensor electrode contingent a change in an environmental condition within a deployment zone when the electrochemical sensor electrode contingent is deployed within the subject's body.

Example A3 includes the sensor device of example A2 or any of examples A1-A45, wherein the change in the environmental condition includes one or more of a change in temperature, a change in moisture, or a change in osmolality.

Example A4 includes the sensor device of example A2 or any of examples A1-A45, wherein the change in the environmental condition includes a change in temperature, and wherein the determined change in temperature is indicative of stability of the temperature within the deployment zone and potential infection at least in or proximate the deployment zone.

Example A5 includes the sensor device of example A2 or any of examples A1-A45, wherein the change in the environmental condition includes a change in temperature, and wherein the determined change in temperature is informative of a magnitude change of the temperature within the deployment zone.

Example A6 includes the sensor device of any of examples A2-A5 or any of examples A1-A45, wherein the determined change in the temperature is compared to a threshold value to generate an alert when the determined change exceeds the threshold value.

Example A7 includes the sensor device of example A2 or any of examples A1-A45, wherein the change in the environmental condition includes a change in osmolality, and wherein the determined change in osmolality is indicative of stability of the salt concentration within the deployment zone and potential dehydration at least in or proximate the deployment zone.

Example A8 includes the sensor device of example A7 or any of examples A1-A45, wherein the determined change in the osmolality is compared to a threshold value to generate an alert when the determined change exceeds the threshold value.

Example A9 includes the sensor device of any of examples A1-A451, further comprising a plurality of electrodes disposed on the substrate and configured to detect a parameter associated with electrical conductivity of the body fluid across at least two electrodes of the plurality of electrodes when the sensor device is deployed within the subject's body.

Example A10 includes the sensor device of example A9 or any of examples A1-A45, wherein the at least two electrodes are configured to operate as an AND gate, such that when the body fluid is in contact with both of the two electrodes, a short circuit occurs across the two electrodes that corresponds to a one and one signal of the AND gate detectable by the sensor device.

Example A11 includes the sensor device of examples A9 or A10 or any of examples A1-A45, wherein at least some electrodes of the plurality of electrodes are at least partially covered by a permeable membrane.

Example A12 includes the sensor device of any of examples A1-A45, wherein the substrate includes an upper surface having a plurality of ridges to provide a three-dimensional profile to the sensor device.

Example A13 includes the sensor device of example A12 or any of examples A1-A45, wherein the substrate is a wafer-based substrate comprising at least one of silicon oxide, germanium, or gallium arsenide.

Example A14 includes the sensor device of examples A12 or A13 or any of examples A1-A45, wherein the electrochemical sensor electrode contingent has a morphology corresponding to the three-dimensional profile.

Example A15 includes the sensor device of example A14 or any of examples A1-A45, wherein the working electrode and the reference electrode are disposed over at least a portion of one or more ridges of the plurality of ridges of the substrate.

Example A16 includes the sensor device of examples A12 or A13 or any of examples A1-A45, wherein the chemical layer has a morphology corresponding to the three-dimensional profile.

Example A17 includes the sensor device of any of examples A1-A45, wherein the reference electrode includes iridium.

Example A18 includes the sensor device of example A17 or any of examples A1-A45, wherein the reference electrode includes iridium oxide.

Example A19 includes the sensor device of examples A17 or A18 or any of examples A1-A45, wherein the sensor device is able to maintain a constant and stable reference signal with respect to the detected electrical signal over a period of time of at least 12 months.

Example A20 includes the sensor device of examples A17 or A18 or any of examples A1-A45, wherein the sensor device is operable to detect the target analyte at a low power consumption based on an applied voltage at the reference electrode of less than 300 mV, or less than 285 mv, or less than 175 mV.

Example A21 includes the sensor device of examples A17 or A18 or any of examples A1-A45, wherein the sensor device is configured to prevent detectable interference signals caused by secondary chemistry elements including dopamine, aspirin, acetaminophen, a numbing chemical for pain treatment, or other.

Example A22 includes the sensor device of any of examples A1-A45, wherein the working electrode includes at least one of platinum, iridium, gold, silver, titanium, single- or multi-walled carbon nanotubes, or an alloy.

Example A23 includes the sensor device of example A22 or any of examples A1-A45, wherein the working electrode includes platinum and iridium.

Example A24 includes the sensor device of any of examples A1-A45, wherein the working electrode is functionalized by the chemical layer configured to interact with the target analyte to facilitate a reaction that results in a change in electrical charge potential or flow at or proximate the surface of the working electrode, such that an electrical signal associated with the reaction is detectable at the working electrode with respect to the reference electrode to measure a parameter associated with the target analyte.

Example A25 includes the sensor device of example A24 or any of examples A1-A45, wherein the chemical layer includes a membrane comprising (i) an outer layer exposed to the body fluid configured to regulate permeation of reactive species including the target analyte and (ii) an inner layer coupled between the outer layer and the surface of the working electrode to immobilize a catalyst able to facilitate the reaction by the permeated reactive species for detection of the target analyte at the working electrode.

Example A26 includes the sensor device of example A24 or any of examples A1-A45, wherein the chemical layer includes a membrane comprising (i) an outer layer exposed to the body fluid configured to regulate permeation of reactive species including the target analyte and (ii) an inner layer coupled between the outer layer and the surface of the working electrode to immobilize a catalyst able to facilitate the reaction by the permeated reactive species for detection of the target analyte at the working electrode, wherein the membrane includes a plurality of ripples on a top surface of the outer layer.

Example A27 includes the sensor device of example A26 or any of examples A1-A45, wherein the membrane includes a thickness of 10 μm or less or of 5 μm to 10 μm.

Example A28 includes the sensor device of example A26 or any of examples A1-A45, wherein the plurality of ripples on the top surface of the outer layer includes a height in a range of 10 μm to 20 μm.

Example A29 includes the sensor device of example A26 or any of examples A1-A45, wherein the plurality of ripples on the top surface of the outer layer are configured to promote functional longevity of electrochemical sensor electrode contingent based on increased signal stability of the detected electrical signal and prevention of fouling of the working electrode.

Example A30 includes the sensor device of any of examples A26-29 or any of examples A1-A45, wherein the plurality of ripples of the membrane are formed at least partially by the membrane conformed on a three-dimensional surface of the substrate.

Example A31 includes the sensor device of any of examples A1-A45, wherein the electronics unit further comprises a signal conditioning unit in communication with the electrochemical sensor electrode contingent via one or more electrical interface components, the signal conditioning unit comprising an electrical circuit configured to process the detected electrical signal by one or more of amplifying the electrical signal, filtering the electrical signal, or converting the electrical signal from analog to digital.

Example A32 includes the sensor device of example A31 or any of examples A1-A45, wherein the electronics unit further comprises a data processing unit in communication with the signal conditioning unit, the data processing unit comprising a processor and a memory and configured to process the electrical signal as data representative of one or more parameters of the target analyte.

Example A33 includes the sensor device of any of examples A1-A45, comprising electrical interconnection wires and electrical interfacing contact sites disposed on the substrate, wherein the electrical interconnection wires are coupled between the electrochemical sensor electrode contingent and the electrical interfacing contact sites.

Example A34 includes the sensor device of example A33 or any of examples A1-A45, wherein the electrical interconnection wires disposed on the substrate are hermetically sealed by a non-permeable material that covers the electrical interconnection wires to provide an electrical shield from the body fluid.

Example A35 includes the sensor device of example A34 or any of examples A1-A45, wherein the non-permeable material includes at least one of a parylene, a urethane, or a Teflon material.

Example A36 includes the sensor device of any of examples A1-A45, comprising a casing that encompasses the electronics unit to protect the electronics unit from exposure to the body fluid and that at least partially encompasses the electrochemical sensor electrode contingent such that the working electrode and reference electrode are exposed to the body fluid when the sensor device is deployed in the body of the subject.

Example A37 includes the sensor device of example A36 or any of examples A1-A45, wherein the casing includes one or both of flat sides or curved sides to provide a form factor of the sensor device.

Example A38 includes the sensor device of example A36 or any of examples A1-A45, wherein the from factor of the sensor device includes at least one of rectangular, a cylindrical, a conical, an elliptical, a pyramidal, a trapezoidal, or a non-uniform shape.

Example A39 includes the sensor device of any of examples A1-A45, comprising a second electrochemical sensor electrode contingent disposed on the substrate and configured to detect a second target analyte in the body fluid when the second electrochemical sensor electrode contingent is deployed fully within the subject's body, the second electrochemical sensor electrode contingent comprising, and optionally consisting of, a second working electrode and a second reference electrode associated with the second working electrode, wherein the second working electrode is functionalized by a second chemical layer configured to facilitate a reaction involving the second target analyte that produces a second electrical signal at the second electrochemical sensor electrode contingent.

Example A40 includes the sensor device of any of examples A1-A45, comprising one or more electrically conductive pads disposed on the substrate configured to be electrically stimulated so as to detect parameters associated with the body fluid exposed to the electrochemical sensor electrode contingent.

Example A41 includes the sensor device of example A40 or any of examples A1-A45, wherein the one or more electrically conductive pads are capable of ensuring the detected electrical signal is detected in a fluid rich environment.

Example A42 includes the sensor device of example A40 or any of examples A1-A45, wherein the one or more electrically conductive pads are capable of decreasing noise associated with the detected signal to a negligible level.

Example A43 includes the sensor device of any of examples A1-A45, wherein the target analyte includes one or more of glucose, oxygen, a ketone, water, an amino acid, a nucleic acid, a lipid, a protein, a carbohydrate, a liposome, a nanoparticle, or a pharmacological drug.

Example A44 includes the sensor device of any of examples A1-A45, wherein the sensor device is configured to detect the target analyte as a primary biomarker indicative of the subject's health and to detect a secondary biomarker concurrently with the primary biomarker, wherein the secondary biomarker includes a physiological parameter including one or both of temperature and vibration, wherein the physiological parameter is detected based on signal analysis of the detected electrical signal by the electrochemical sensor electrode contingent.

Example A45 includes the sensor device of any of examples A1-A44, wherein the sensor device is operable to be inserted below a subcutaneous layer of a subject and within interstitial pocket of the subject such that the sensor contingent is able to detect and determine whether there is a sufficient pool of interstitial fluid in the interstitial pocket to obtain the electrical signal associated with the target analyte.

In some embodiments in accordance with the present technology (example A46), a sensor device for in vivo or ex vivo monitoring of analytes includes a substrate comprising an electrically non-conductive material, wherein the substrate is a wafer-based substrate comprising silicon oxide and includes an upper surface having a plurality of ridges to provide a three-dimensional profile to the sensor device; an electrochemical sensor electrode contingent disposed on the substrate and configured to detect a target analyte in a body fluid when the electrochemical sensor electrode contingent is deployed fully within a subject's body, the electrochemical sensor electrode contingent comprising, and optionally consisting of, a working electrode and a reference electrode associated with the working electrode, wherein the electrochemical sensor electrode contingent has a morphology corresponding to the three-dimensional profile provided by the substrate, wherein the working electrode is functionalized by a chemical layer configured to facilitate a reaction involving the target analyte that produces an electrical signal at the electrochemical sensor electrode contingent, wherein the reference electrode includes iridium oxide and the working electrode includes platinum and iridium, and wherein the sensor device is operable to detect the target analyte at a low power consumption based on an applied voltage at the reference electrode of less than 300 mV, or less than 285 mv, or less than 175 mV, wherein the chemical layer includes a membrane comprising (i) an outer layer exposed to the body fluid configured to regulate permeation of reactive species including the target analyte and (ii) an inner layer coupled between the outer layer and the surface of the working electrode to immobilize a catalyst able to facilitate the reaction by the permeated reactive species for detection of the target analyte at the working electrode, wherein the membrane includes a plurality of ripples on a top surface of the outer layer; a plurality of electrodes disposed on the substrate and configured to detect a parameter associated with electrical conductivity of the body fluid across at least two electrodes of the plurality of electrodes when the sensor device is deployed within the subject's body, wherein the at least two electrodes are configured to operate as an AND gate, such that when the body fluid is in contact with both of the two electrodes, a short circuit occurs across the two electrodes that corresponds to a one and one signal of the AND gate detectable by the sensor device; and an electronics unit in communication with the electrochemical sensor electrode contingent, the electronics unit comprising a wireless communications unit including a wireless transmitter or wireless transceiver to transmit data associated with the electrical signal to an external processor, wherein, the processor is operable to determine a parameter associated with the target analyte based on the electrical signal measured at the electrochemical sensor electrode contingent, and wherein the processor is configured to determine from the same electrical signal produced at the electrochemical sensor electrode contingent a change in an environmental condition including temperature within a deployment zone when the electrochemical sensor electrode contingent is deployed within the subject's body.

Example A47 includes the sensor device of example A46, wherein the sensor device includes at least one feature in any of examples A2-A45.

In some embodiments in accordance with the present technology (example A48), a sensor device for in vivo or ex vivo monitoring of analytes includes a substrate comprising an electrically non-conductive material; and an electrochemical sensor electrode contingent disposed on the substrate and configured to detect a target analyte in a body fluid when the electrochemical sensor electrode contingent is deployed fully within a subject's body, the electrochemical sensor electrode contingent comprising, and optionally consisting of, a working electrode and a reference electrode associated with the working electrode, wherein the working electrode is functionalized by a chemical layer configured to facilitate a reaction involving the target analyte that produces an electrical signal at the electrochemical sensor electrode contingent; and an electronics unit in communication with the electrochemical sensor electrode contingent, the electronics unit comprising a wireless communications unit including a wireless transmitter or wireless transceiver to transmit data associated with the electrical signal to an external processor.

Example A49 includes the sensor device of example A46, wherein the sensor device includes at least one feature in any of examples A2-A45.

In some embodiments in accordance with the present technology (example A50), a sensor device for in vivo or ex vivo monitoring of analytes includes a substrate comprising an electrically non-conductive material; and an electrochemical sensor electrode contingent disposed on the substrate and configured to detect a target analyte in a body fluid when the electrochemical sensor electrode contingent is deployed fully within a subject's body, the electrochemical sensor electrode contingent comprising a working electrode and a reference electrode associated with the working electrode, wherein the working electrode is functionalized by a chemical layer configured to facilitate a reaction involving the target analyte that produces an electrical signal at the electrochemical sensor electrode contingent.

Example A51 includes the sensor device of example A50, wherein the sensor device includes one or more features recited in any of examples A2-A45.

In some embodiments in accordance with the present technology (example A52), a system for analyte and environment sensing includes a sensor device and a data processing system. The sensor device is operable to be deployed at least partially in a body of a patient user, the sensor device comprising a substrate comprising an electrically non-conductive material, an electrochemical sensor electrode contingent disposed on the substrate and configured to detect a target analyte in a body fluid when the electrochemical sensor electrode contingent is deployed fully within a patient user's body, the electrochemical sensor electrode contingent comprising, and optionally consisting of, a working electrode and a reference electrode associated with the working electrode, wherein the working electrode is functionalized by a chemical layer configured to facilitate a reaction involving the target analyte that produces an electrical signal at the electrochemical sensor electrode contingent, and an electronics unit in communication with the electrochemical sensor electrode contingent, the electronics unit comprising a wireless communications unit including a wireless transmitter or wireless transceiver to transmit data associated with the electrical signal to an external processor. The data processing system comprising a processor and a memory, which the data processing system is in data communication with the sensor device and configured to receive the data from the sensor unit and process the received data to indicate a parameter associated with the target analyte and/or an environmental condition in a region where the electrochemical sensor electrode contingent is deployed.

Example A53 includes the system of any of examples A52-A58, wherein the sensor device includes one or more features associated with the sensor device recited in any of examples A1-A45, any of examples A46-A47, and/or any of examples A48-A49.

Example A54 includes the system of any of examples A52-A58, wherein the data processing system includes a server computer comprising the processor and the memory and one or more databases in data communication with the server computer, wherein the data processing system is configured to remotely monitor data associated with the patient user obtained by the sensor device.

Example A55 includes the system of any of examples A52-A58, further comprising: a receiver device, comprising a processor and a memory, operable to (i) receive a wireless transmission carrying data indicative of the electrical signal acquired from the sensor device and (ii) transmit the data to the data processing system.

Example A56 includes the system of example A55 or any of examples A52-A58, wherein the receiver device is configured to store the data in the memory of the receiver device.

Example A57 includes the system of example A55 or any of examples A52-A58, wherein the receiver device is in communication with the data processing system via a network of computers in communication with each other and accessible through the Internet.

Example A58 includes the system of any of examples A52-A57, further comprising: a remote client computing device, comprising a processor and a memory, in data communication with the data processing system and configured to receive processed data that is selected, filtered, and/or formatted by the data processing system.

CONCLUSION

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed are techniques and structures as described and shown, including:

1. A sensor device for in vivo monitoring of analytes, comprising:
   a substrate comprising an electrically non-conductive material, wherein the substrate is a wafer-based substrate comprising silicon oxide and includes an upper surface having a plurality of ridges to provide a three-dimensional profile to the sensor device;
   an electrochemical sensor electrode contingent disposed on the substrate and configured to detect a target analyte in a body fluid when the electrochemical sensor electrode contingent is deployed fully within a subject's body, the electrochemical sensor electrode contingent comprising, and optionally consisting of, a working electrode and a reference electrode associated with the working electrode, wherein the electrochemical sensor electrode contingent has a morphology corresponding to the three-dimensional profile provided by the substrate, wherein the working electrode is functionalized by a chemical layer configured to facilitate a reaction involving the target analyte that produces an electrical signal at the electrochemical sensor electrode contingent, wherein the reference electrode includes iridium oxide and the working electrode includes platinum and iridium, and wherein the sensor device is operable to detect the target analyte at a low power consumption based on an applied voltage at the reference electrode of greater than or equal to about 110 mV and less than 300 mV, less than 285 mv, or less than 175 mV,
   wherein the chemical layer includes a membrane comprising (i) an outer layer exposed to the body fluid configured to regulate permeation of reactive species including the target analyte and (ii) an inner layer coupled between the outer layer and the surface of the working electrode to immobilize a catalyst able to facilitate the reaction by the permeated reactive species for detection of the target analyte at the working electrode, wherein the membrane includes a plurality of ripples on a top surface of the outer layer;
   a plurality of electrodes disposed on the substrate and configured to detect a parameter associated with electrical conductivity of the body fluid across at least two electrodes of the plurality of electrodes when the sensor device is deployed within the subject's body, wherein the at least two electrodes are configured to operate as an AND gate, such that when the body fluid is in contact with both of the two electrodes, a short circuit occurs across the two electrodes that corresponds to a one and one signal of the AND gate detectable by the sensor device; and
   an electronics unit in communication with the electrochemical sensor electrode contingent, the electronics unit comprising a wireless communications unit including a wireless transmitter or wireless transceiver to transmit data associated with the electrical signal to an external processor,
   wherein, the external processor is operable to determine a parameter associated with the target analyte based on the electrical signal measured at the electrochemical sensor electrode contingent, and wherein the processor is configured to determine from the same electrical signal produced at the electrochemical sensor electrode contingent a change in an environmental condition including temperature within a deployment zone when the electrochemical sensor electrode contingent is deployed within the subject's body.

2. The sensor device of claim 1, wherein the determined change in temperature is indicative of stability of the temperature within the deployment zone and potential infection at least in or proximate the deployment zone.

3. The sensor device of claim 1, wherein the determined change in temperature is compared to a threshold value to generate an alert when the determined change exceeds the threshold value.

4. The sensor device of claim 1, wherein the determined change in the environmental condition includes a change in osmolality.

5. The sensor device of claim 1, wherein at least some electrodes of the plurality of electrodes are at least partially covered by a permeable membrane.

6. The sensor device of claim 1, wherein the working electrode and the reference electrode are disposed over at least a portion of one or more ridges of the plurality of ridges of the substrate.

7. The sensor device of claim 1, wherein the chemical layer has a morphology corresponding to the three-dimensional profile.

8. The sensor device of claim 1, wherein the reference electrode includes iridium.

9. The sensor device of claim 1, wherein the sensor device is able to maintain a constant and stable reference signal with respect to the detected electrical signal over a period of time of at least 12 months.

10. The sensor device of claim 1, wherein the sensor device is configured to prevent detectable interference signals caused by secondary chemistry elements including dopamine, aspirin, acetaminophen, or a numbing chemical for pain treatment.

11. The sensor device of claim 1, wherein the working electrode further includes at least one of gold, silver, titanium, single- or multi-walled carbon nanotubes, or an alloy.

12. The sensor device of claim 1, wherein the working electrode is functionalized by the chemical layer configured to interact with the target analyte to facilitate a reaction that results in a change in electrical charge potential or flow at or proximate the surface of the working electrode, such that an electrical signal associated with the reaction is detectable at the working electrode with respect to the reference electrode to measure a parameter associated with the target analyte.

13. The sensor device of claim 12, wherein the chemical layer includes (i) an outer layer exposed to the body fluid configured to regulate permeation of reactive species including the target analyte and (ii) an inner layer coupled between the outer layer and the surface of the working electrode to immobilize a catalyst able to facilitate the reaction by the permeated reactive species for detection of the target analyte at the working electrode.

14. The sensor device of claim 1, wherein the membrane includes a thickness of 10 μm or less or of 5 μm to 10 μm.

15. The sensor device of claim 1, wherein the plurality of ripples on the top surface of the outer layer includes a height in a range of 10 μm to 20 μm.

16. The sensor device of claim 1, wherein the plurality of ripples on the top surface of the outer layer are configured to promote functional longevity of electrochemical sensor electrode contingent based on increased signal stability of the detected electrical signal and prevention of fouling of the working electrode.

17. The sensor device of any of claim 1, wherein the plurality of ripples of the membrane are formed at least partially by the membrane conformed on a three-dimensional surface of the substrate.

18. The sensor device of claim 1, wherein the electronics unit further comprises a signal conditioning unit in communication with the electrochemical sensor electrode contingent via one or more electrical interface components, the signal conditioning unit comprising an electrical circuit configured to process the detected electrical signal by one or more of amplifying the electrical signal, filtering the electrical signal, or converting the electrical signal from analog to digital.

19. The sensor device of claim 18, wherein the electronics unit further comprises a data processing unit in communication with the signal conditioning unit, the data processing unit comprising a processor and a memory and configured to process the electrical signal as analyte data representative of one or more parameters of the target analyte.

20. The sensor device of claim 1, comprising electrical interconnection wires and electrical interfacing contact sites disposed on the substrate, wherein the electrical interconnection wires are coupled between the electrochemical sensor electrode contingent and the electrical interfacing contact sites.

21. The sensor device of claim 20, wherein the electrical interconnection wires disposed on the substrate are hermetically sealed by a non-permeable material that covers the electrical interconnection wires to provide an electrical shield from the body fluid.

22. The sensor device of claim 21, wherein the non-permeable material includes at least one of a parylene, a urethane, or a Teflon material.

23. The sensor device of claim 1, comprising a casing that encompasses the electronics unit to protect the electronics unit from exposure to the body fluid and that at least partially encompasses the electrochemical sensor electrode contingent such that the working electrode and reference electrode are exposed to the body fluid when the sensor device is deployed in the body of the subject.

24. The sensor device of claim 23, wherein the casing includes one or both of flat sides or curved sides to provide a form factor of the sensor device.

25. The sensor device of claim 23, wherein the from factor of the sensor device includes at least one of rectangular, a cylindrical, a conical, an elliptical, a pyramidal, a trapezoidal, or a non-uniform shape.

26. The sensor device of claim 1, comprising:
a second electrochemical sensor electrode contingent disposed on the substrate and configured to detect a second target analyte in the body fluid when the second electrochemical sensor electrode contingent is deployed fully within the subject's body, the second electrochemical sensor electrode contingent comprising, and optionally consisting of, a second working electrode and a second reference electrode associated with the second working electrode, wherein the second working electrode is functionalized by a second chemical layer configured to facilitate a reaction involving the second target analyte that produces a second electrical signal at the second electrochemical sensor electrode contingent.

27. The sensor device of claim 1, comprising:
one or more electrically conductive pads disposed on the substrate configured to be electrically stimulated so as to detect parameters associated with the body fluid exposed to the electrochemical sensor electrode contingent.

28. The sensor device of claim 27, wherein the one or more electrically conductive pads are capable of ensuring the detected electrical signal is detected in a fluid rich environment, and/or are capable of decreasing noise associated with the detected signal to a negligible level.

29. The sensor device of claim 1, wherein the target analyte comprises glucose.

* * * * *